United States Patent [19]

Tomesch

[11] Patent Number: 4,820,718
[45] Date of Patent: Apr. 11, 1989

[54] N-ALKYL-(2- OR 5-SUBSTITUTED-2-METHOXYCARBONYL AMINOALKYL FURANYL)-SUBSTITUTED CYCLIMMONIUM SALTS AND USE THEREOF IN PAF INHIBITION

[75] Inventor: John C. Tomesch, Succasunna, N.J.
[73] Assignee: Sandoz Pharm. Corp., Hanover, N.J.
[21] Appl. No.: 98,350
[22] Filed: Sep. 17, 1987
[51] Int. Cl.$^4$ .................... C07D 401/00; A61K 31/44
[52] U.S. Cl. ..................................... 514/336; 546/283
[58] Field of Search ......................... 546/283; 514/336

[56] References Cited

U.S. PATENT DOCUMENTS 4,711,892 12/1987 Manoury et al. ................... 546/283

Primary Examiner—Mary C. Lee
Assistant Examiner—Robert C. Whittenbaugh
Attorney, Agent, or Firm—Gerald D. Sharkin; Robert S. Honor; Joseph J. Borovian

[57] ABSTRACT

The invention discloses certain N-alkyl-(2- or 5-substituted-2-methoxycarbonyl aminoalkyl furanyl)-substituted cyclimmonium salts useful as PAF inhibitors, pharmaceutical compositions containing said compounds as an active ingredient thereof and a method of using such compositions for inhibiting PAF-induced blood platelet aggregation, PAF-mediated bronchoconstriction and extravasation, PAF-induced hypotension, PAF-induced ischemic bowel disease and PAF-mediated, endotoxin-induced lung injury.

21 Claims, No Drawings

N-ALKYL-(2- OR 5-SUBSTITUTED-2-METHOXYCARBONYL AMINOALKYL FURANYL)-SUBSTITUTED CYCLIMMONIUM SALTS AND USE THEREOF IN PAF INHIBITION

The present invention relates to certain N-alkyl-(2- or 5-substituted-2-methoxycarbonyl aminoalkyl furanyl)-substituted cyclimmonium salts and to their use as inhibitors of PAF-induced blood platelet aggregation. The invention also relates to pharmaceutical compositions containing the aforementioned compounds as an active ingredient thereof and to the method of using such composition for inhibiting PAF-mediated bronchoconstriction and extravasation, PAF-induced hypotension, PAF-involved ischemic bowel disease and PAF-mediated, endotoxin-induced lung injury. In addition, the invention relates to a select group of said compounds which appears to exhibit a long duration of PAF inhibition.

Blood platelets, also called thrombocytes, are well recognized as important cellular elements that circulate in the blood. Their role is to staunch bleeding by forming clots in broken blood vessels, i.e., they are nature's corks. They have, however, been implicated in a variety of immunologically mediated forms of tissue injury. Their participation in these processes involved the release of platelet activating factor (PAF) which in turn interacts with the platelets, inducing aggregation and secretion of granular constituents. As a further consequence of platelet activation, there may result a fatal reaction consisting of acute pulmonary hypertension, right heart dilation, systemic hypotension, significant increases in pulmonary vascular resistance, a decrease in dynamic lung compliance and often complete pulmonary apnea. More recently, evidence has been obtained which appears to implicate platelet activating factor in the formation of fibromuscular lesions of the arterial walls of the aorta and coronary arteries, thereby contributing to the development of atherosclerosis. Further, the possible role of PAF in ischemic bowel disease, particularly necrotizing enterocolitis (NEC) has recently been described, thereby implicating PAF in the development of disorders leading to bowel necrosis. Still further, evidence has been obtained which supports the hypothesis that PAF is an important mediator of endotoxin-induced lung injury, -pulmonory hypertension, -hypoxemia and -reduced cardiac output.

The existence of platelet activating factor was proposed in an article by Henson, P. M., Journal of Experimental Medicine 131, 287 (1970). However, due to the limited quantities of material available for study, great difficulty was encountered in defining the chemical structure and biochemical activity of PAF.

One of the earlier reports on the chemical nature of PAF was that of Benveniste, J., Nature 249, 581 (1974), wherein the physiochemical characteristics of PAF were reported. A later study of Benveniste, J. et al., Nature 269, 170 (1977) reported on the purification of PAF isolated by successive thin layer chromatography. A more recent study by Hanahan, et al. in the J. of Biol. Chem. 225; 5514–5516 (June 1980) confirmed that the compounds, 1-O-alkyl-2-acetyl-sn-glyceryl-3-phosphoryl-choline (AGEPC), and PAF are one and the same composition. Since that time, many research endeavors have been directed to the synthesis of compounds structurally related to that of PAF in an effort to uncover compounds useful in the inhibition of platelet activating factor.

The essence of the present invention is the discovery that certain N-alkyl-(2- or 5-substituted-2-methoxycarbonyl aminoalkyl furanyl)-substituted cyclimmonium salts of formula I:

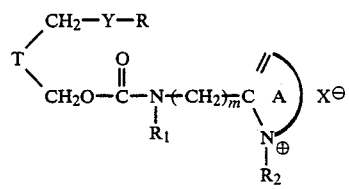

wherein T is a group of the formula (a)

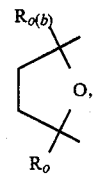

or a group of the formula (b)

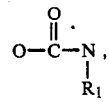

where both $R_o$'s are the same and are either hydrogen or methyl;

Y is —O— or

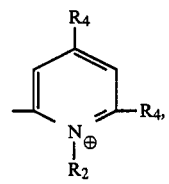

R is n-$C_{12}$–$C_{20}$ alkyl, alkenyl or alkynyl;
each $R_1$, independently, is hydrogen, acetyl, pivaloyl, benzoyl or $C_1$–$C_4$ alkyl;
m is an integer 1 to 8;
A, together with the quaternary nitrogen atom and the carbon atom, forms a pyridinium group of the formula

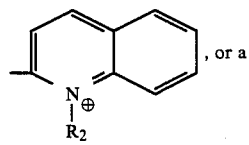

a quinolinium group of the formula

, or a thiazolium group of the formula

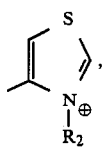

where
R$_2$ is methyl or ethyl; and each R$_4$, independently, is hydrogen or methyl; and
X$^\ominus$ is chloride, bromide, iodide or C$_1$-C$_4$ alkylsulfonate;

are useful as inhibitors of PAF-induced blood platelet aggregation.

Of the compounds of formula I, preferred are compounds of formula Ia:

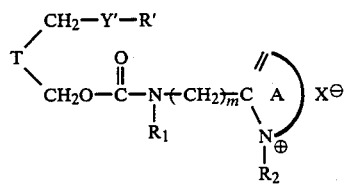

wherein
T, m, A, R$_1$, R$_2$ and X$^\ominus$ are as defined above;
Y' is

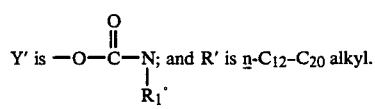

and
R' is n-C$_{12}$-C$_{20}$ alkyl.

The more preferred compounds of formula I are those of formula Ib:

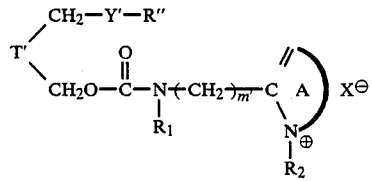

where
Y', R$_1$, A, R$_2$ and X$^\ominus$ are as defined above;
T' is a group of formula (a) as defined above;
R''is n-C$_{14}$-C$_{20}$alkyl; and
m' is an integer 1 to 5.

The even more preferred compounds of formula I are those of formula Ic:

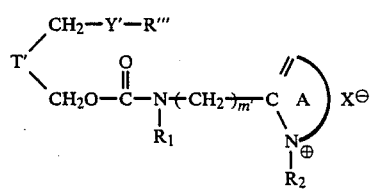

where
T', Y', R$_1$, m', A, R$_2$ and X$^\ominus$ are as defined above; and

R''' is n-C$_{16}$-C$_{20}$ alkyl.

Another aspect of the instant invention is the discovery that the compounds of formula Ic are especially useful as PAF inhibitors in that they exhibit a long duration of PAF inhibition.

The compounds of formula I where Y is —O—, R$_1$ is hydrogen, X$^\ominus$ is bromide, iodide or C$_1$-C$_4$ alkylsulfonate and T, R, m, A and R$_2$ are as defined above may be prepared by the following reaction scheme:

REACTION A

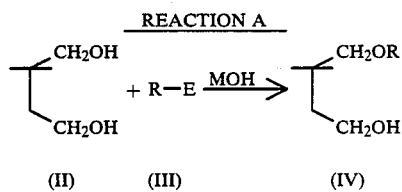

where E is chloride, bromide, iodide, arylsulfonate (e.g., phenylsulfonate or toluenesulfonate) or C$_{1-4}$ alkylsulfonate (e.g., methylsulfonate), M is an alkali metal or alkaline earth metal and T and R are as defined above.

REACTION B

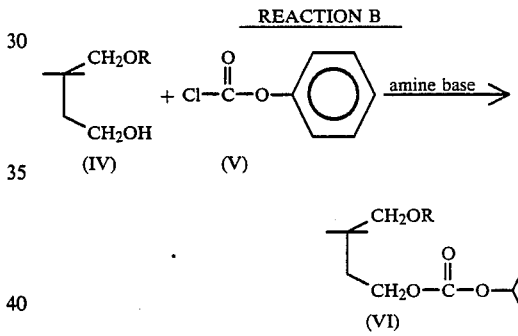

where T and R are as defined above.

REACTION C

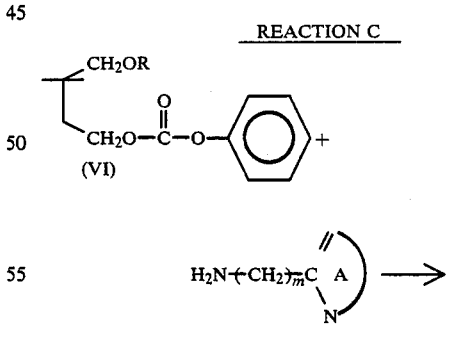

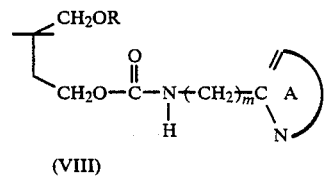

where T, R, m and A are as defined above.

REACTION D

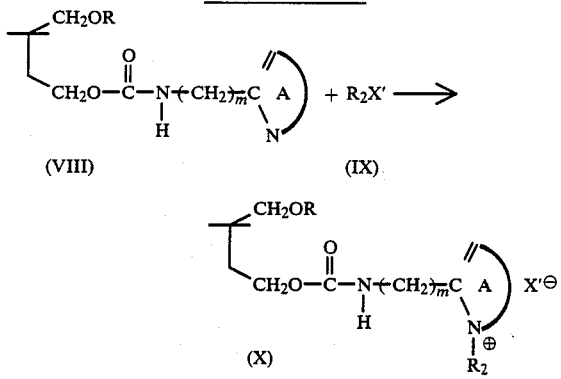

where X' is bromide, iodide or $C_1$–$C_4$ alkylsulfonate and T, R, m, A and $R_2$ are as defined above.

With respect to the individual reactions, Reaction A concerns the reaction of a diol of formula II with a compound of formula III in the presence of an alkali metal or alkaline earth metal hydroxide to yield a compound of formula IV. The reaction may conveniently be carried out in an inert, organic solvent, e.g., an aromatic hydrocarbon such as benzene, toluene and the like, or a cyclic ether such as tetrahydrofuran or dioxane, or in the presence of a polar, aprotic solvent such as dimethylsulfoxide, dimethylformamide or dimethylacetamide. Optionally, the reaction may be conducted in the presence of a phase-transfer catalyst, e.g., tetrabutyl ammonium bisulfate. Although the temperature and time of the reaction are not critical, the reaction is typically carried out at a temperature of from 20° to 80° C. for a period of beetween 1 and 24 hours.

Reaction B involves the reaction of a compound produced in Reaction A, i.e., a compound of formula IV, with the compound of formula V, viz., phenyl chloroformate, in the presence of an amine base, such as pyridine or triethylamine to yield a phenylcarbonate compound of formula VI. The reaction is conveniently carried out in an inert, organic solvent, e.g., an aromatic hydrocarbon such as toluene, benzene or xylene, a halogenated, aliphatic hydrocarbon such as methylene chloride, chloroform or carbon tetrachloride, or an ether such as diethyl ether. The reaction may be carried out at temperatures of from 0° to 70° C. for a period of between 5 and 30 hours.

Reaction C concerns the reaction of a compound produced in Reaction B, i.e., a phenyl carbonate compound of formula VI, with a compound of formula VII to yield a cyclimmonium compound of formula VIII. The reaction may be conveniently carried out in an inert, organic solvent, e.g., an aromatic hydrocarbon such as benzene, toluene and the like, a cyclic ether such as tetrahydrofuran or dioxane or a halogenated, aliphatic hydrocarbon such as methylene chloride, chloroform or carbon tetrachloride. The reaction is typically carried out at a temperature of from 20° to 80° C. for a period of between 1 and 24 hours.

The last reaction, viz., Reaction D, is directed to the alkylation of a compound produced in Reaction C, i.e., a cyclimmonium compound of formula VIII, with a large excess of an alkylating agent of formula IX. The alkylation reaction is optionally conducted in the presence of an inert, organic solvent, e.g., a halogenated, aliphatic hydrocarbon such as dichloromethane, at a temperature of from 25° C. to the reflux temperature of the alkylating agent for a period of between 24 and 168 hours to yield a compound of formula X.

When it is desired to prepare the corresponding chloride salt of a compound of formula X, an acidic ion exchange resin with chloride present is utilized to exchange the chloride ion for the bromide, iodide or $C_1$–$C_4$ alkylsulfonate anion prepared in Reaction D. The exchange reaction is conveniently carried out in an inert, organic solvent, e.g., a $C_1$–$C_4$ alkanol such as methanol, or a mixture of a $C_1$–$C_4$ alkanol and water.

The compounds of formula I where Y is —O—, $R_1$ is other than hydrogen, $X^\ominus$ is bromide, iodide or $C_1$–$C_4$ alkylsulfonate and T, R, m, A and $R_2$ are as defined above may be prepared essentially as described below employing a compound of formula VIII as the starting material;

STEP A

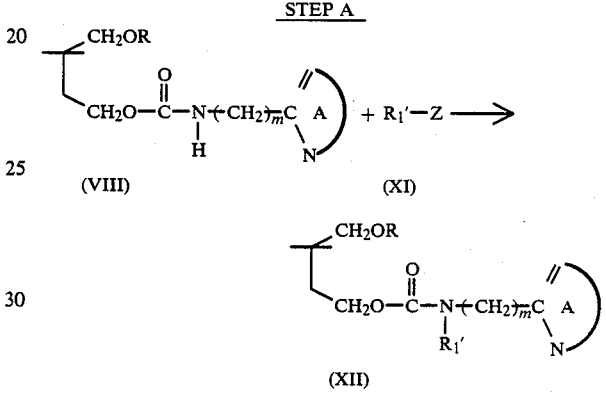

where $R_1'$ is acetyl, pivaloyl, benzoyl or $C_1$–$C_4$ alkyl, Z is chloride or bromide and, when $R_1'$ is acetyl, Z may additionally be acetate, and T, R, m and A are as defined above.

STEP B

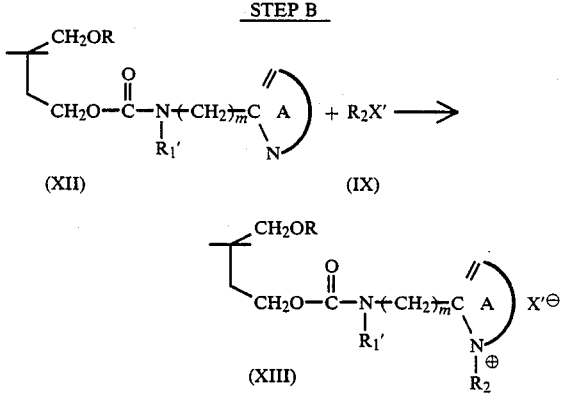

where T, R, m, A, $R_1'$, $R_2$ and X' are as defined above.

Step A concerns the reaction of a compound of formula VIII with a compound of formula XI containing a leaving group Z, to yield a compound of formula XII. Optionally, the reaction may be conducted in the presence of an amine base such as triethylamine and/or a catalyst such as 4-dimethylamino pyridine. The reaction is conveniently carried out in an inert, organic solvent, e.g., an aromatic hydrocarbon such as benzene or toluene, a halogenated, aliphatic hydrocarbon such as methylene chloride, chloroform or carbon tetrachloride, or a cyclic ether such as tetrahydrofuran or dioxane. The reaction is typically carried out at a temperature of from 20° to 80° C. for a period of between 20 and 96 hours.

As to Step B for preparing a compound of formula XIII, it is conducted in an analogous manner to that set forth above in Reaction D for preparing a compound of formula X.

Moreover, the corresponding chloride salt of a compound of formula XIII may be prepared by the exchange reaction described above for preparing a chloride salt of a compound of formula X.

When a compound of formula I is desired where Y is —O—, $R_1$ is $C_1$-$C_4$ alkyl, $X^\ominus$ is bromide, iodide or $C_1$-$C_4$ alkylsulfonate and T, R, m, A and $R_2$ are as defined above, it has been found more desirable to employ a three-step reaction essentially as set forth below utilizing a compound of formula IV as the starting material:

STEP 1

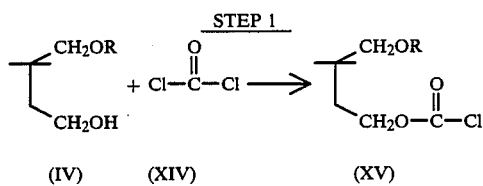

(IV)   (XIV)   (XV)

where T and R are as defined above.

STEP 2

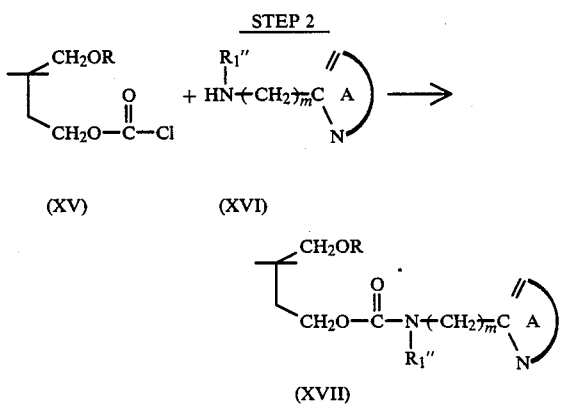

(XV)   (XVI)

(XVII)

where $R_1''$ is $C_1$-$C_4$ alkyl, and T, R, m and A are as defined above.

STEP 3

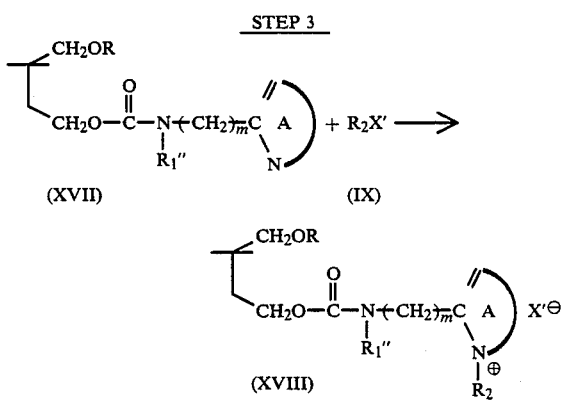

(XVII)   (IX)

(XVIII)

where T, R, m, A, $R_1''$, $R_2$ and X' are as defined above.

In Step 1, a compound of formula IV is reacted with a three- to ten-fold excess of the compound of formula XIV, viz., phosgene, in toluene to yield a compound of formula XV. The reaction is conveniently carried out in an inert, organic solvent, e.g., an aromatic hydrocarbon such as benzene, toluene or xylene, or a halogenated, aliphatic hydrocarbon such as methylene chloride, chloroform or carbon tetrachloride. The reaction is typically carried out at a temperature of from −10° to 40° C. for a period of between 1 and 12 hours.

Step 2 concerns the reaction of a compound produced in Step 1, i.e., a compound of formula XV, with a substituted 2-aminoalkyl heteroaromatic compound of formula XVI in the presence of an amine base such as triethyl amine or an alkali metal bicarbonate such as sodium bicarbonate to yield a cyclimmonium compound of the formula XVII. The reaction may be conveniently carried out in an inert, organic solvent, e.g., an aromatic hydrocarbon such as benzene, toluene or xylene, or halogenated, aliphatic hydrocarbon such as methylene chloride, chloroform or carbon tetrachloride. The reaction is typically carried out a temperature of from 20° to 80° C. for a period of between 2 and 30 hours.

As to Step 3 for preparing a compound of formula XVIII, it is conducted in an analogous manner to Reaction D described above for preparing a compound of formula X.

The compounds of formula I where Y is

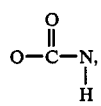

$R_1$ is hydrogen, $X^\ominus$ is bromide, iodide or $C_1$-$C_4$ alkylsulfonate and T, R, m, A and $R_2$ are as defined above may be prepared as indicated below:

REACTION AA

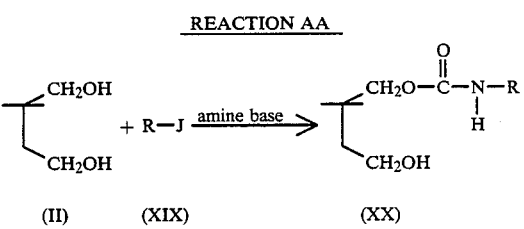

(II)   (XIX)   (XX)

where J is an isocyanate group and T and R are as defined above.

REACTION BB

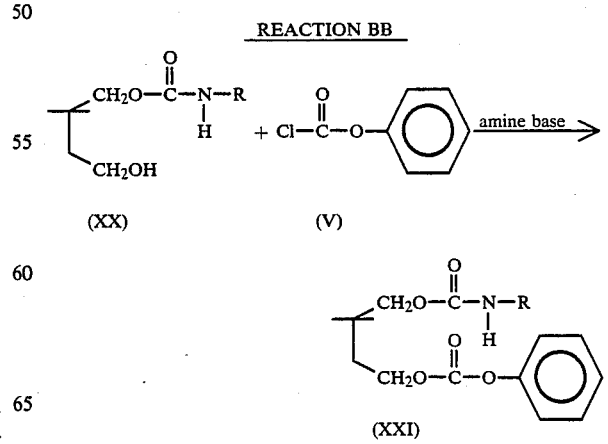

(XX)   (V)

(XXI)

where T and R are as defined above.

REACTION CC

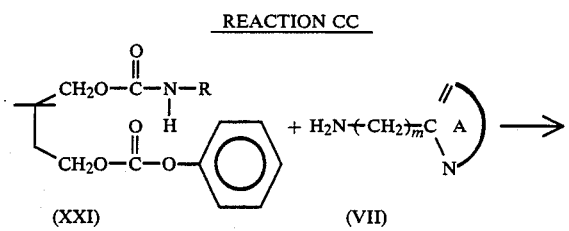

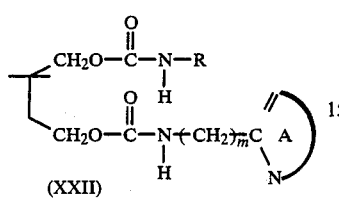

where T, R, m and A are as defined above.

REACTION DD

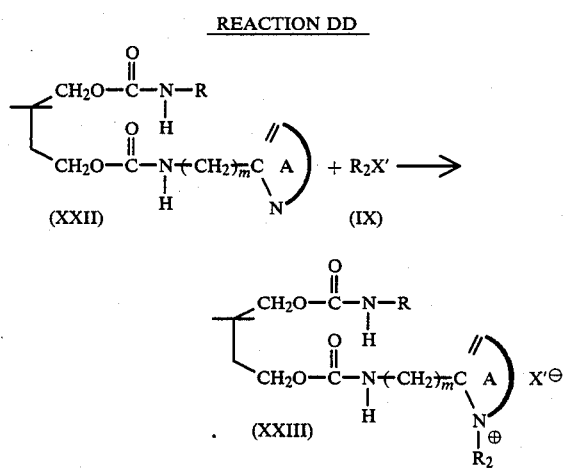

where T, R, m, A, $R_2$ and X' are as defined above.

In considering the reactions individually, Reaction AA involves the reaction of a diol of formula II with a compound of formula XIX, i.e., an appropriate isocyanate compound containing the residue, R, in the presence of an amine base such as pyridine or triethylamine, to yield a compound of formula XX. The reaction may optionally be conducted in the presence of a cosolvent which may be an aromatic hydrocarbon such as benzene or toluene, an aromatic halohydrocarbon such as chlorobenzene, an aliphatic halohydrocarbon such as chloroform or dichloromethane, a dialkyl ether such as diethylether, a cyclic ether such as tetrahydrofuran or a dialkyl amide such as dimethylformamide. The reaction is typically carried out at a temperature of from 20° to 100° C. for a period of between 1 and 24 hours.

As to Reactions BB, CC and DD for preparing a compound of formulae XXI, XXII and XXIII, respectively, they are conducted in an identical manner to that set forth above in Reactions B, C and D.

Moreover, the corresponding chloride salt of a compound of formula XXIII may be prepared by the exchange reaction described above for preparing a chloride salt of a compound of formula X.

The compounds of formula I where Y is

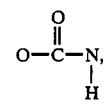

$R_1$ is other than hydrogen, $X^\ominus$ is bromide, iodide or $C_1$-$C_4$-alkylsulfonate and T, R, m, A and $R_2$ are as defined above may be prepared as set forth below employing a compound of formula XXII as the starting material.

STEP AA

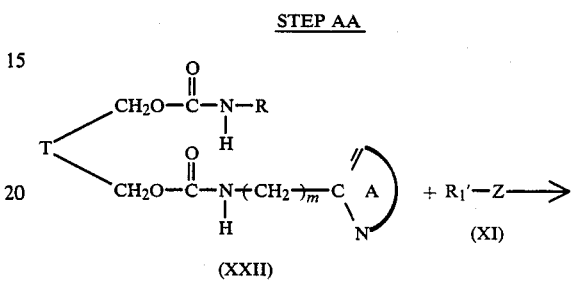

where R, R, m, A, $R_1'$ and Z are as defined above.

STEP BB $$\text{(XXIV)} + R_2X' \longrightarrow \text{(XXV)}$$

(CH2O-C(=O)-N(R)H and CH2O-C(=O)-N(R_1')-(CH2)_m-C-A-N⊕-R_2, X'⊖)

where R, T, m, A, $R_1'$, $R_2$ and X' are as defined above.

As to Step AA for preparing a compound of formula XXIV, it is conducted in an identical manner to Step A set forth above for preparing a compound of formula XII.

Concerning Step BB for preparing a compound of formula XXV, it is conducted in an analogous manner to Reaction D described above for preparing a compound of formula X.

Moreover, the corresponding chloride salt of a compound of formula XXV may be prepared by the exchange reaction described above for preparing a chloride salt of a compound of formula X.

When a compound of formula I is desired where Y is

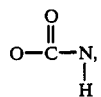

$R_1$ is $C_1$-$C_4$ alkyl, $X^\ominus$ is bromide, iodide or $C_1$-$C_4$-alkylsulfonate, and T, R, m, A and $R_2$ are as defined above, it has been found more desirable to employ a three-step reaction essentially as set forth below utilizing a compoound of formula XX as the starting material:

REACTION AAA

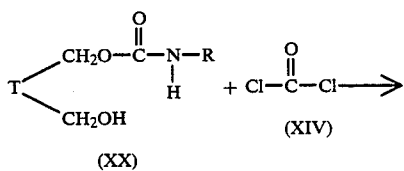

where R and T are as defined above.

REACTION BBB

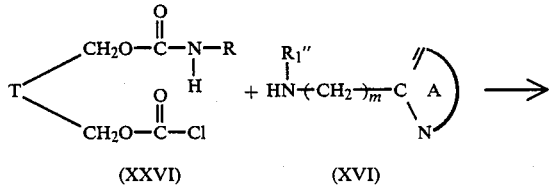

where R, T, m, A and $R_1''$ are as defined above.

REACTION CCC

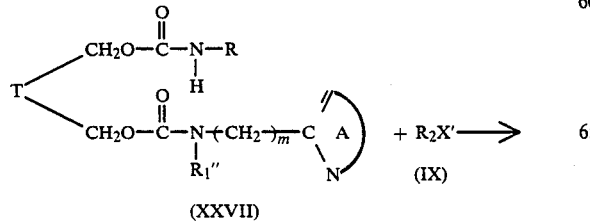

-continued
REACTION CCC

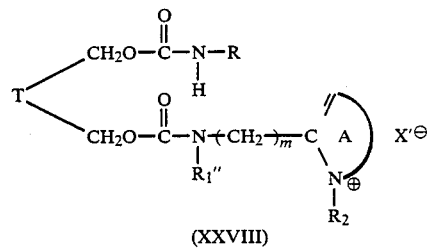

where R, T, m, A, $R_1''$, $R_2$ and $X'$ are as defined above.

With regard to Reactions AAA, BBB and CCC for preparing a compound of formulae XXVI, XXVII and XXVIII, respectively, they are conducted in an identical manner to that set forth above in Steps 1, 2 and 3.

The compounds of formula I where Y is

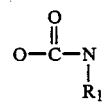

where $R_1$ is other than hydrogen or $C_1$-$C_4$-alkyl, the other $R_1$ is hydrogen, $X^\ominus$ is bromide, iodide or $C_1$-$C_4$-alkylsulfonate and T, R, m, A and $R_2$ are as defined above may be prepared as illustrated below:

STEP 1A

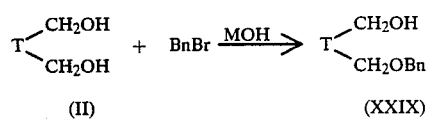

where Bn is benzyl, and T and M are as defined above.

STEP 2A

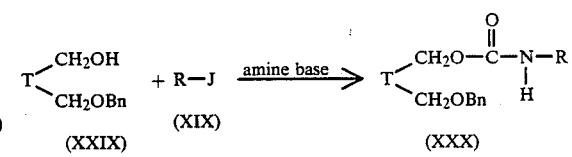

where T, R, J and Bn are as defined above.

STEP 3A

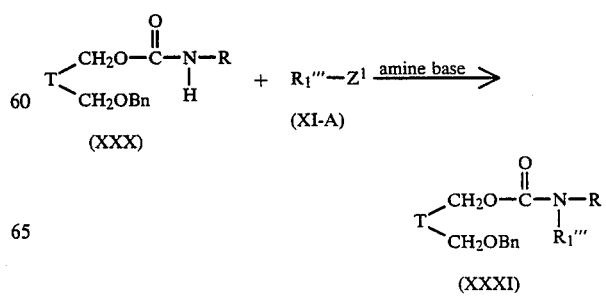

where $R_1'''$ is acetyl, pivaloyl or benzoyl, $Z^1$ is chloride or bromide, and T, R and Bn are as defined above.

STEP 4A

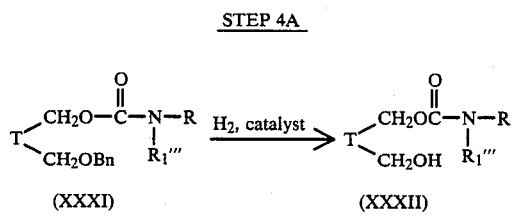

where T, R, $R_1'''$ and Bn are as defined above.

STEP 5A

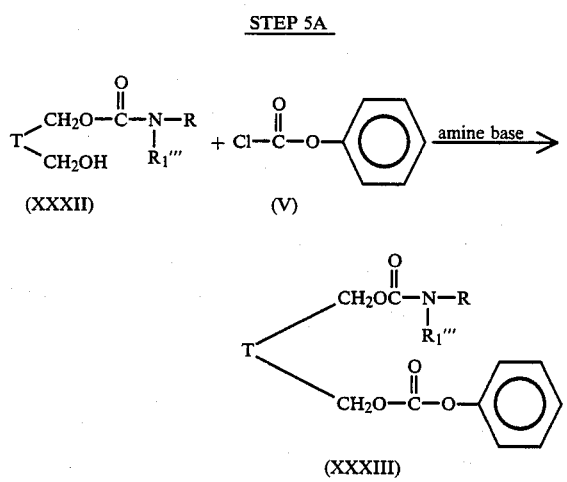

where T, R and $R_1'''$ are as defined above.

STEP 6A

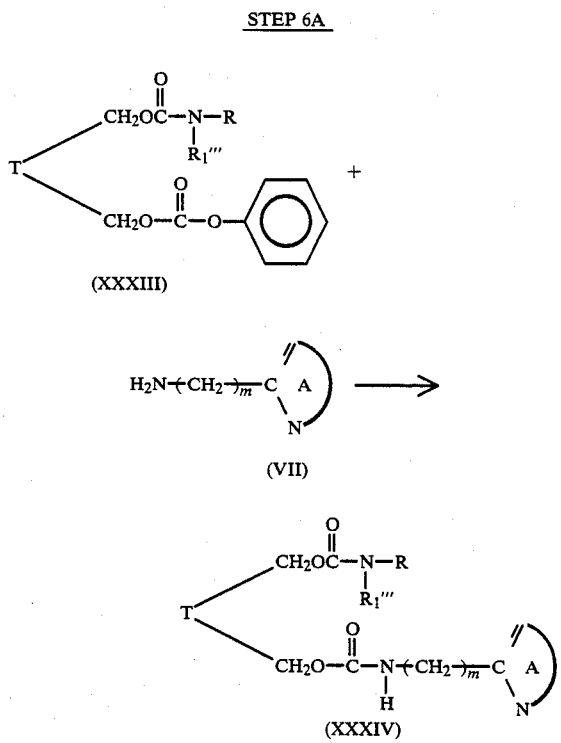

where T, R, $R_1'''$, m and A are as defined above.

STEP 7A

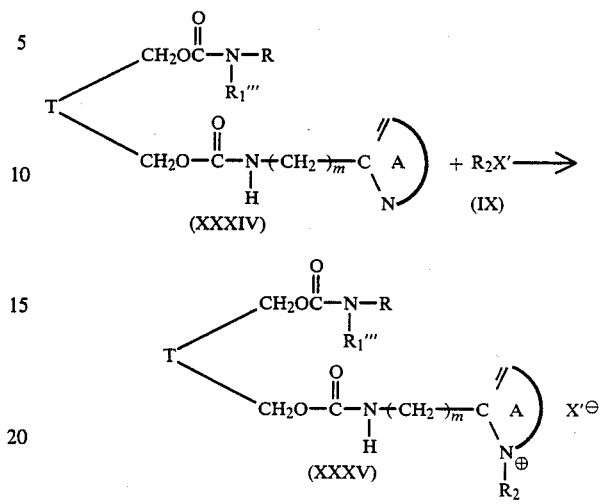

where T, R, $R_1'''$, m, A and $R_2$ and X' are as defined above.

In considering the steps individually, Step 1A concerns the reaction of a diol of formula II with benzyl bromide in the presence of an alkali metal or alkaline earth metal hydroxide to yield a compound of formula XXIX. The reaction may conveniently be carried out in an inert, organic solvent, e.g., an aromatic hydrocarbon such as benzene, toluene and the like, or a cyclic ether such as tetrahydrofuran or dioxane, or in the presence of a polar, aprotic solvent such as dimethylsulfoxide, dimethyl-formamide or dimethylacetamide. Optionally, the reaction may be conducted in the presence of a phase-transfer catalyst, e.g., tetrabutyl ammonium bromide. Although the temperature and time of the reaction are not critical, the reaction is typically carried out at a temperature of from 20° to 80° C. for a period of between 1 and 24 hours.

As to Step 2A for preparing a compound of formula XXX, it is conducted in an identical manner to that set forth above in Reaction AA.

Step 3A involves the reaction of a benzyl ether carbamate compound produced in Step 2A, i.e., a compound of formula XXX, with an acyl chloride or bromide of formula XI-A in the presence of an amine base such as triethylamine and/or a catalyst such as 4-dimethylamino pyridine to yield a compound of formula XXXI. The reaction is conveniently carried out in the presence of an inert, organic solvent, e.g., an aromatic hydrocarbon such as benzene or toluene, a halogenated, aliphatic hydrocarbon such as chloroform or carbon tetrachloride, or a cyclic ether such as tetrahydrofuran or dioxane. As to reaction temperatures and times, the reaction is initially conducted at room temperature over a period of between 1 and 24 hours, then at the reflux temperature of the solvent for a period of between 1 and 24 hours and during which time the amine base is added to the reaction.

Step 4A concerns the hydrogenolysis of the benzyl ether group of a compound produced in Step 3A, i.e., a compound of formula XXXI, by dissolving said compound in a lower alkanol, e.g., methanol, ethanol and the like, with palladium on carbon and subjecting the resultant mixture to a pressure of between 15 to 50 lbs. of hydrogen gas at a temperature of from 20° to 50° C.

for a period of between 5 and 24 hours to yield a compound of formula XXXII.

As to Steps 5A, 6A and 7A for preparing a compound of formulae XXXIII, XXXIV and XXXV, respectively, they are conducted in an analogous fashion to that set forth above in Reactions B, C and D.

Moreover, the corresponding chloride salt of a compound of formula XXXV may be prepared by the exchange reaction described above for preparing a chloride salt of a compound of formula X.

The compounds of formula I where Y is

where $R_1$ is $C_1$-$C_4$ alkyl, the other $R_1$ is hydrogen, $X^{\ominus}$ is bromide, iodide or $C_1$-$C_4$ alkylsulfonate, and T, R, m, A and $R_2$ are as defined above may be prepared according to the following reaction scheme utilizing a compound of formula XXX as the starting material:

REACTION 1A

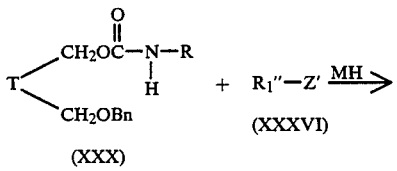

where T, R, Bn, $R_1''$, $Z^1$ and M are as defined above.

REACTION 2A

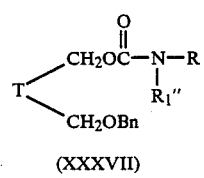

where T, R, Bn and $R_1''$ are as defined above.

REACTION 3A

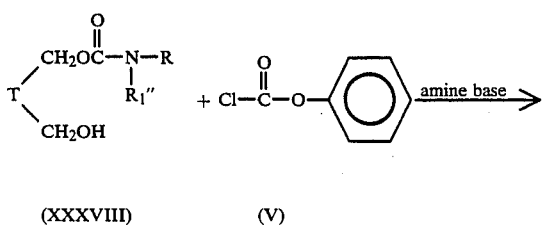

-continued
REACTION 3A

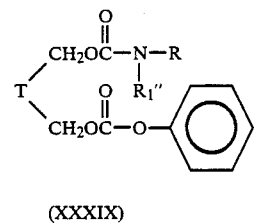

where T, R and $R_1''$ are as defined above.

REACTION 4A

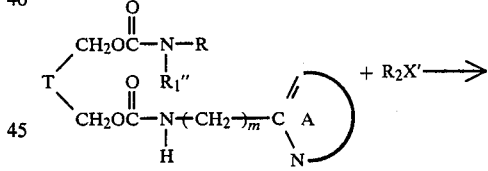

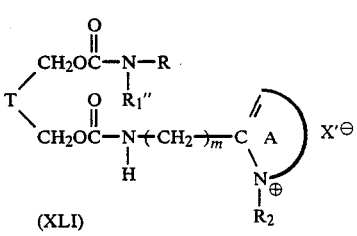

where T, R, $R_1''$, m and A are as defined above.

REACTION 5A

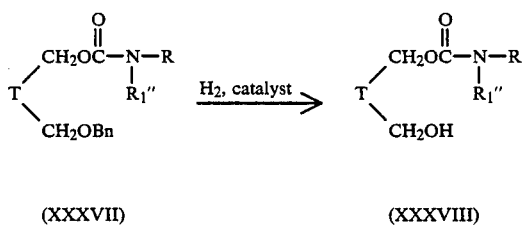

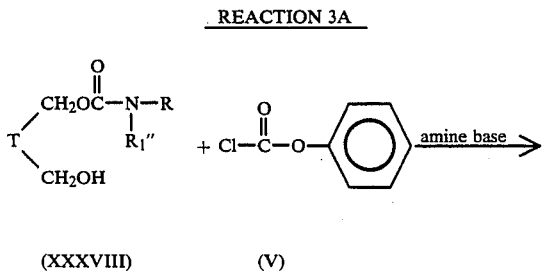

where T, R, $R_1''$, m, A, $R_2$ and X' are as defined above.

With regard to the reactions individually, Reaction 1A involves the reaction of a benzyl ether carbamate compound of formula XXX with a $C_1$-$C_4$ alkyl chloride or bromide compound of formula XXXVI in the presence of an alkali metal or alkaline earth metal hydride, preferably an alkali metal hydride such as potassium or sodium hydride to yield a compound of formula XXXVII. The reaction is conveniently carried out in an inert, organic solvent, e.g., aromatic hydrocarbon such as benzene or toluene, a di-$C_1$-$C_3$ alkyl ether such as diethyl ether or a cyclic ether such as tetrahydrofuran or dioxane. The reaction is typically carried out at a temperature of from 20° to 60° C. for a period of between 2 and 48 hours.

As to Reaction 2A, which is directed to the hydrogenolysis of the benzyl ether group of a compound produced in Reaction 1A, i.e., a compound of formula XXXVII, it is conducted in an identical manner to that set forth above in Step 4A.

With regard to Reactions 3A, 4A and 5A for preparing a compound of formulae XXXIX, XL and XLI, respectively, they are conducted in an analogous manner to that set forth above in Reactions B, C and D.

Moreover, the corresponding chloride salt of a compound of formula XLI may be prepared by the exchange reaction described above for preparing a chloride salt of a compound of formula X.

The compounds of formula I where Y is

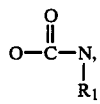

where $R_1$ is other than hydrogen or $C_1$-$C_4$ alkyl, the other $R_1$ is other than hydrogen, $X^{\ominus}$ is bromide, iodide or $C_1$-$C_4$-alkylsulfonate, and T, R, m, A and $R_2$ are as defined above may be prepared as depicted below employing a compound of formula XXXIV as the starting material:

STEP AAA

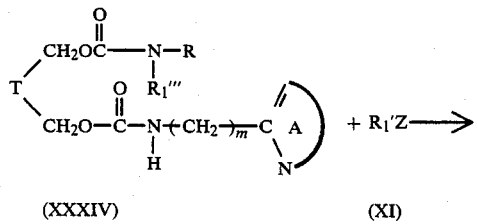

(XXXIV)  (XI)

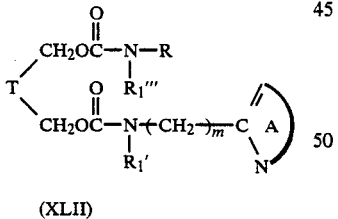

(XLII)

where T, R, $R_1'''$, m, A, $R_1'$ and Z are as defined above.

STEP BBB

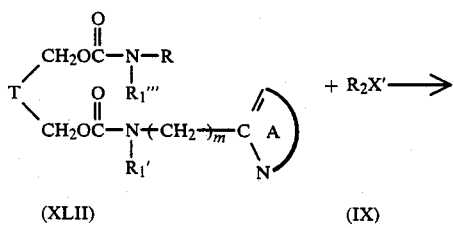

(XLII)  (IX)

-continued
STEP BBB

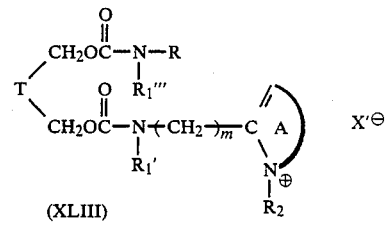

(XLIII)

where T, R, $R_1'''$, $R_1'$, m, A, $R_2$ and X' are as defined above.

With regard to Steps AAA and BBB for preparing a compound of formulae XLII and XLIII, respectively, they are conducted in an essentially identical number to that set forth above in Steps A and B.

Moreover, the corresponding chloride salt of a compound of formula XLIII may be prepared by the exchange reaction described above for preparing a chloride salt of a compound of formula X.

When a compound of formula I is desired where Y is

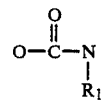

where $R_1$ is other than hydrogen or $C_1$-$C_4$ alkyl, the other $R_1$ is $C_1$-$C_4$ alkyl, $X^{\ominus}$ is bromide, iodide or $C_1$-$C_4$-alkylsulfonate, and T, R, m, A and $R_2$ are as defined above, it has been found more desirable to employ a three step reaction employing a compound of formula XXXII as the starting material. By reacting said compound with the compound of formula XIV as described above in Step 1, and utilizing a compound so produced in carrying out the reactions described above in Steps 2 and 3, results in a compound having the formula

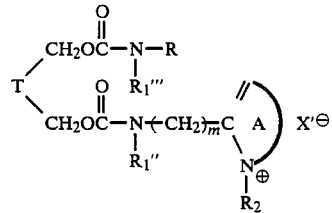

The compounds of formula I where Y is

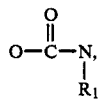

where $R_1$ is $C_1$-$C_4$ alkyl, the other $R_1$ is other than hydrogen, $X^{\ominus}$ is bromide, iodide or $C_1$-$C_4$ alkylsulfonate, and T, R, m, A and $R_2$ are as defined above may be prepared as illustrated below employing a compound of formula XL is the starting material:

STEP AAAA

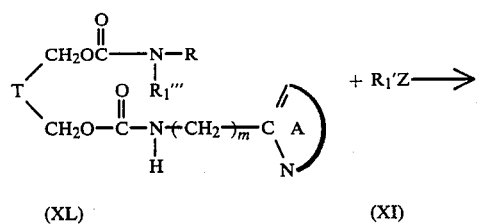

(XL)   (XI)

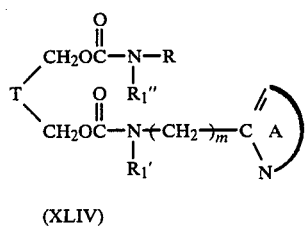

(XLIV)

where T, R, $R_1''$, m, A, $R_1'$ and Z are as defined above.

STEP BBBB

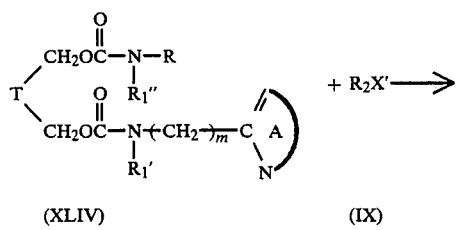

(XLIV)   (IX)

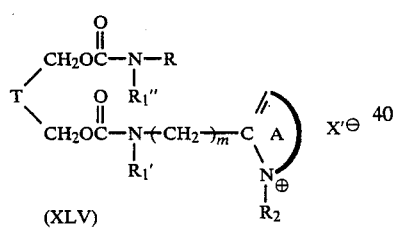

(XLV)

With regard to Steps AAAA and BBBB for preparing a compound of formulae XLIV and XXLV, respectively, they are conducted in an essentially identical manner to that set forth above in Steps A and B.

Moreover, the corresponding chloride salt of a compound of formula XLV may be prepared by the exchange reaction described above for preparing a chloride salt of a compound of formula X.

When a compound of formula I is desired where Y is

where $R_1$ is $C_1$-$C_4$ alkyl, the other $R_1$ is $C_1$-$C_4$alkyl, $X^\ominus$ is bromide, iodide or $C_1$-$C_4$ alkylsulfonate, and T, R, m, A and $R_2$ are as defined above, it has been found more desirable to employ a three step reaction employing a compound of formula XXXVIII as the starting material. By reacting said compound with the compound of formula XIV as described above in Step 1, and utilizing a compound so produced in carrying out the reactions described above in Steps 2 and 3, results in a compound having the formula

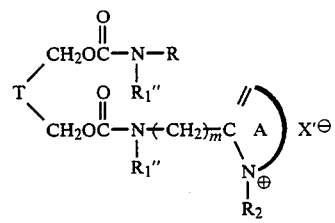

The compounds of formula I where Y is

(i.e., the inverse carbamates), $R_1$ is hydrogen, $X^\ominus$ is bromide, iodide or $C_1$-$C_4$ alkylsulfonate, and T, R, m, A and $R_2$ are as defined above may be prepared as illustrated below employing a compound of formula XXIX as the starting material:

REACTION 1B

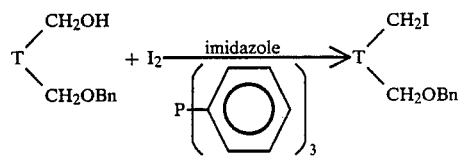

(XXIX)   (XLVI)

where T and Bn are as defined above.

REACTION 2B

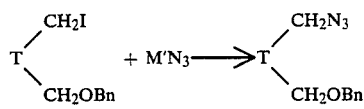

(XLVI)   (XLVII)

where $M^1$ is an alkali metal, and T and Bn are as defined above.

REACTION 3B

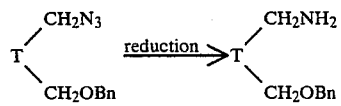

(XLVII)   (XLVIII)

where T and Bn are as defined above.

REACTION 4B

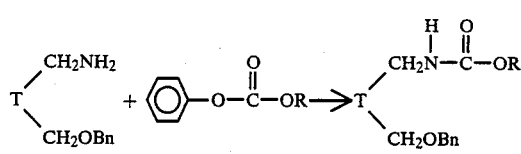

(XLVIII) (XLIX) (L)

where T, Bn and R are as defined above.

REACTION 5B

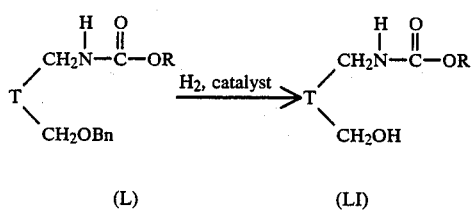

(L) (LI)

where T, Bn and R are as defined above.

REACTION 6B

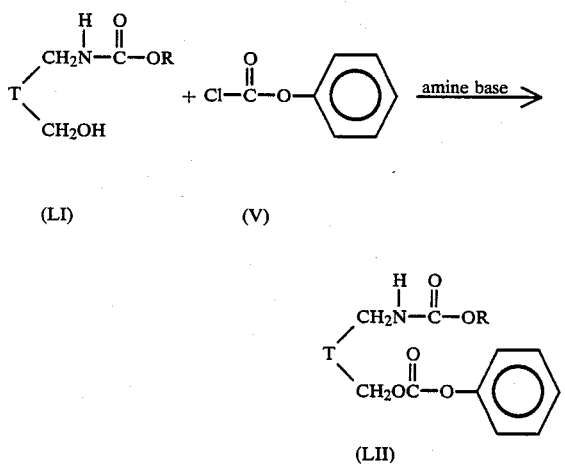

(LI) (V)

(LII)

where T and R are as defined above.

REACTION 7B

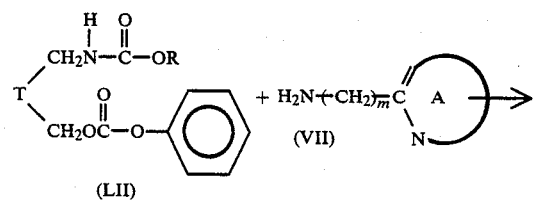

(LII)

REACTION 7B (continued)

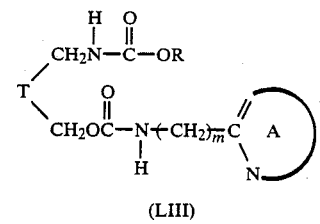

(LIII)

where T, R, m and A are as defined above.

REACTION 8B

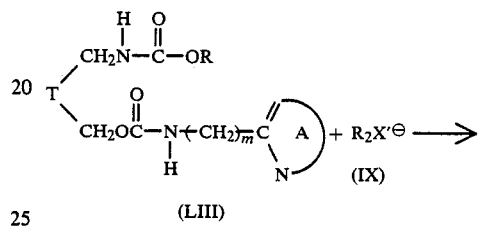

(LIII)

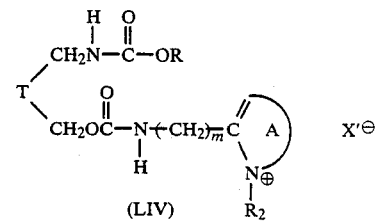

(LIV)

where T, R, m, A, $R_2$ and X' are as defined above.

In considering the individual reactions, Reaction 1B concerns the reaction of a compound of formula XXIX with iodine in the presence of triphenylphosphine and imidazole to yield an iodide compound of formula XLVI. This reaction is conducted in the presence of an inert, organic solvent, e.g., an aromatic hydrocarbon such as benzene, toluene and the like, and at a temperature of from 0° to 80° C. for a period of 1 to 4 hours.

In Reaction 2B, a compound produced in Reaction 1B, i.e., an iodide compound of formula XLVI, is reacted with an alkali metal azide such as sodium azide to produce a compound of formula XLVII. This reaction is conveniently carried out in water containing a phase-transfer catalyst such as tetrabutyl ammonium bromide, or the reaction may be conducted in a polar, aprotic solvent such as dimethyl sulfoxide or dimethyl formamide. Although the reaction temperatures and times are not critical, the reaction is typically carried out at a temperature of from 20° to 100° C. for a period of from 2 to 24 hours.

Reaction 3B involves the reduction of an azide group of a compound produced in Reaction 2B, i.e., a compound of formula XLVII, by dissolving said compound in a lower alkanol, e.g., methanol, ethanol and the like, with palladium on calcium carbonate poisoned with lead acetate (Lindlar's catalyst) and subjecting the resultant mixture to a pressure of between 15 and 50 lbs. of hydrogen gas at a temperature of from 20° to 30° C. for a period of between 1 and 5 hours to yield a compound of formula XLVIII.

In Reaction 4B, a compound produced in Reaction 3B, i.e., an amine compound of formula XLVIII, is reacted with a phenyl carbonate compound of formula XLIX to yield a compound of formula L. The reaction may conveniently be carried out in an inert, organic solvent, e.g., an aromatic hydrocarbon such as benzene, toluene and the like, a halogenated, aliphatic hydrocarbon such as methylene chloride, chloroform or carbon tetrachloride, or a cyclic ether such as tetrahydrofuran or dioxane. The reaction is typically carried out at a temperature of from 20° to 90° C. for a period of from 1 to 48 hours.

Reaction 5B concerns the hydrogenolysis of the benzyl ether group of a compound produced in Reaction 4B, i.e., a compound of formula L. The reaction, which yields a compound of formula LI, is conducted in an identical manner to Step 4A set forth above.

As to Reactions 6B, 7B and 8B for preparing a compound of formulae LII, LIII and LIV, respectively, they are conducted in an analogous manner to that set forth above in Reactions B, C and D.

Moreover, the corresponding chloride salt of a compound of formula LIV may be prepared by the exchange reaction described above for preparing a chloride salt of a compound of formula X.

The compounds of formula I where Y is

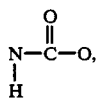

$R_1$ is other than hydrogen, $X^{\ominus}$ is bromide, iodide or $C_1$–$C_4$-alkylsulfonate, and T, R, m, A and $R_2$ are as defined above may be prepared in the following manner employing a compound of formula LIII as the starting material:

STEP 1B

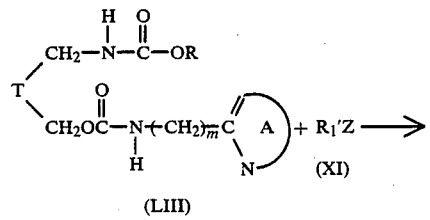

(LIII)

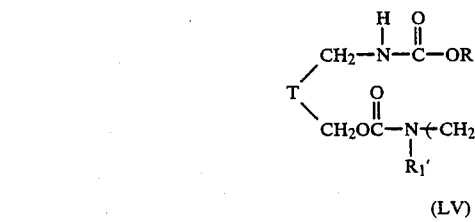

(LV)

where R, T, m, A, $R_1'$ and Z are as defined above.

STEP 2B

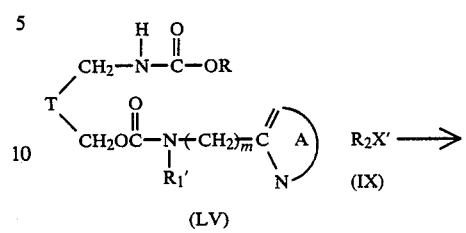

(LV)

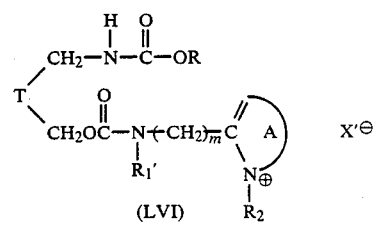

(LVI)

where R, T, m, A, $R_1'$, $R_2$ and X' are as defined above.

With regard to Step 1B for preparing a compound of formula LV, it is conducted in an identical manner to Step A set forth above for preparing a compound of formula XII.

As to Step 2B for preparing a compound of formula LVI, it is conducted analogously to Reaction D described above for preparing a compound of formula X.

Moreover, the corresponding chloride salt of a compound of formula LVI may be prepared by the exchange reaction described above for preparing a chloride salt of a compound of formula X.

When a compound of formula I is desired where Y is

$R_1$ is $C_1$–$C_4$ alkyl, $X^{\ominus}$ is bromide, iodide or $C_1$–$C_4$-alkylsulfonate, and T, R, m, A and $R_2$ are as defined above, it has been found more desirable to employ a three-step reaction essentially as depicted below utilizing a compound of formula LI as the starting material:

REACTION 1C

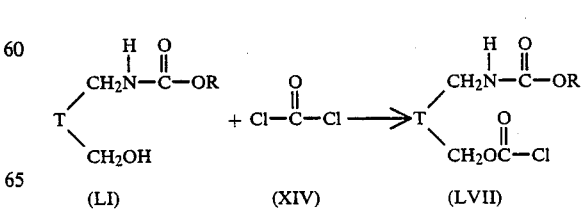

(LI)    (XIV)    (LVII)

where R and T are as defined above.

REACTION 2C

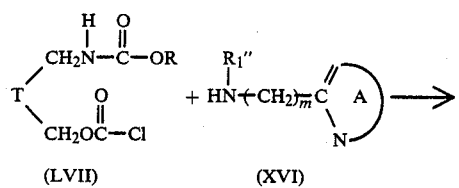

(LVII)     (XVI)

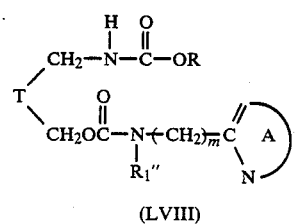

(LVIII)

where R, T, $R_1''$, m and A are as defined above.

REACTION 3C

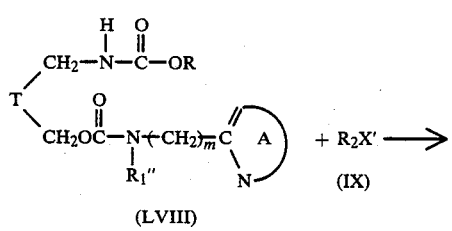

(LVIII)     (IX)

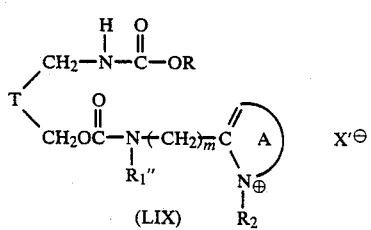

(LIX)

where R, T, $R_1''$, m, A, $R_2$ and X' are as defined above.

With respect to Reactions 1C, 2C and 3C for preparing a compound of formulae LVII, LVIII and LIX, respectively, they are conducted in an analogous manner to that set forth above in Steps 1, 2 and 3.

The compounds of formula I where Y is

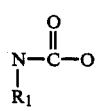

where $R_1$ is other than hydrogen or $C_1$-$C_4$ alkyl, the other $R_1$ is hydrogen, $X^\ominus$ is bromide, iodide or $C_1$-$C_4$ alkylsulfonate and T, R, m, A and $R_2$ are as defined above may be prepared as depicted below employing a compound of formula L as the starting material:

STEP 1C

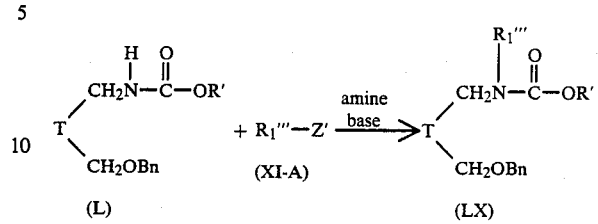

(L)     (XI-A)     (LX)

where R, T, Bn, $R_1'''$ and $Z^1$ are as defined above.

STEP 2C

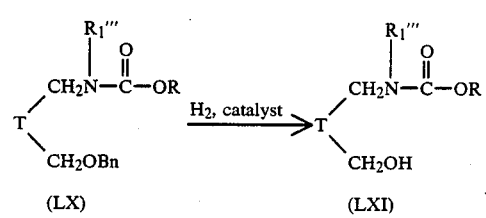

(LX)     (LXI)

where R, T, Bn and $R_1'''$ are as defined above.

STEP 3C

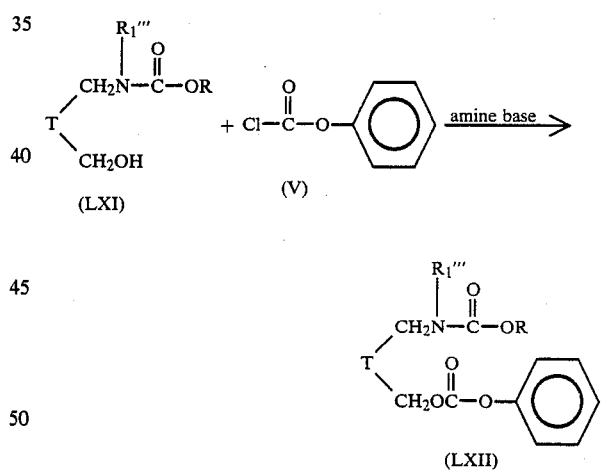

(LXI)     (V)

(LXII)

where R, T and $R_1'''$ are as defined above.

STEP 4C

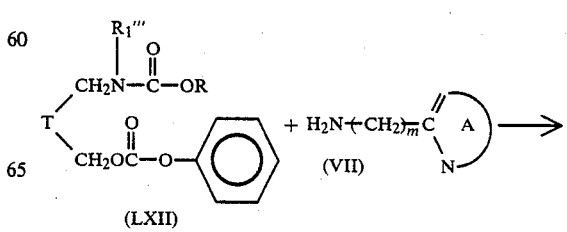

(LXII)     (VII)

-continued
STEP 4C

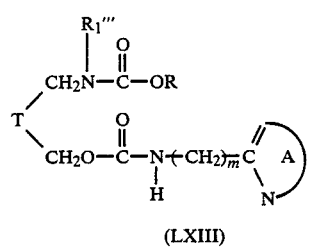

(LXIII)

where R, T, $R_1'''$, m and A are as defined above.

STEP 5C

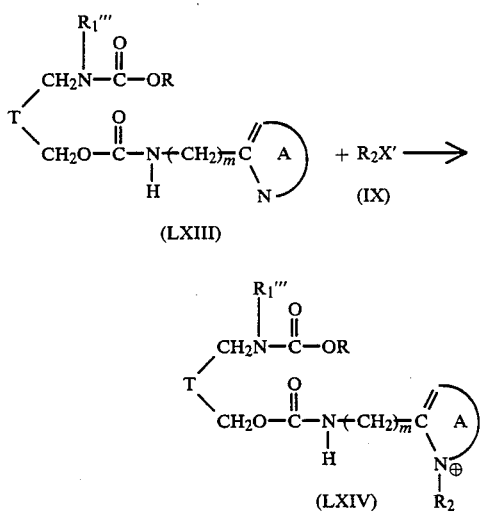

where R, T, $R_1'''$, m, A, $R_2$ and X' are as defined above.

As to the reaction conditions (i.e., solvents, catalysts, temperatures, times, etc.) regrding Steps 1C–5C for preparing the compounds of formulae LX, LXI, LXII, LXIII and LXIV, respectively, they are conducted in an analogous manner to Steps 3A through 7A described above.

Moreover, the corresponding chloride salt of a compound of formula LXIV may be prepared by the exchange reaction described above for preparing a chloride salt of a compound of formula X.

The compounds of formula I where Y is

where $R_1$ is $C_1$–$C_4$ alkyl, the other $R_1$ is hydrogen, $X^\ominus$ is bromide, iodide or $C_1$–$C_4$ alkylsulfonate, and T, R, m, A and $R_2$ are as defined above may be prepared according to the following reaction scheme utilizing a compound of formula L as the starting material:

REACTION AAAA

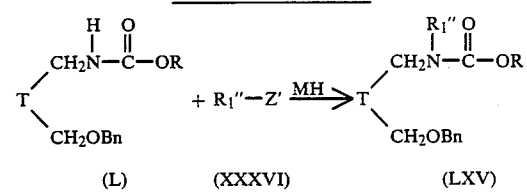

where R, T, Bn, $R_1''$, Z' and M are as defined above.

REACTION BBBB

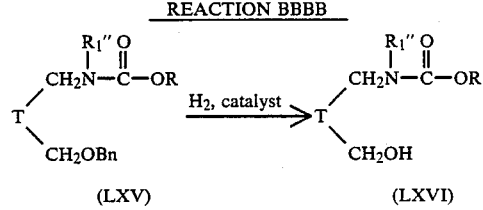

where R, T, Bn and $R_1''$ are as defined above.

REACTION CCCC

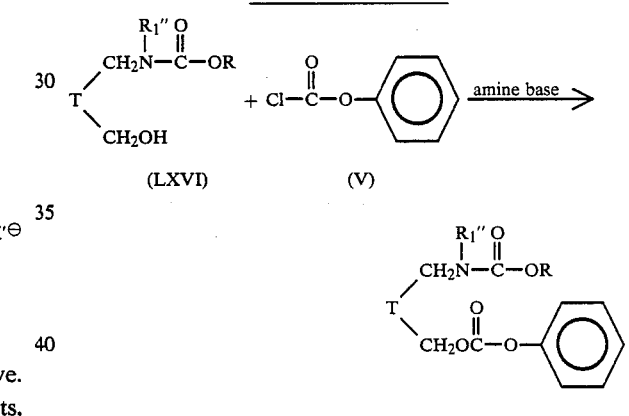

where R, T and $R_1''$ are as defined above.

REACTION DDDD

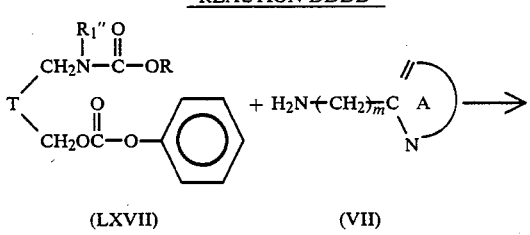

where R, T, $R_1''$, m and A are as defined above.

REACTION EEEE

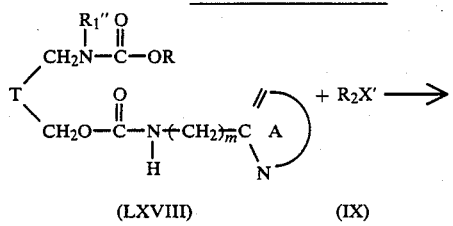

(LXVIII)     (IX)

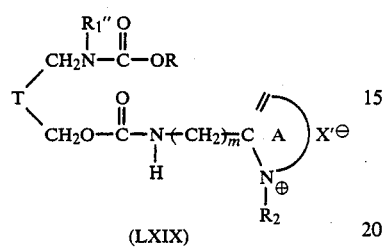

(LXIX)

where R, T, $R_1''$, m, A, $R_2$ and X' are as defined above.

As to the reaction conditions (i.e., times, temperatures, solvents, etc.) involving Reactions AAAA-EEEE for preparing the compounds of formulae LXV, LXVI, LXVII, LXVIII and LXIX, respectively, they are conducted in an identical manner to Reactions 1A through 5A described above.

Moreover, the corresponding chloride salt of a compound of formula LXIX may be prepared by the exchange reaction described above for preparing a chloride salt of a compound of formula X.

The compounds of formula I where Y is

where $R_1$ is other than hydrogen or $C_1$–$C_4$ alkyl, the other $R_1$ is other than hydrogen, $X^\ominus$ is bromide, iodide or $C_1$–$C_4$ alkyl-sulfonate, and T, R, m, A and $R_2$ are as defined above may be prepared as depicted below employing a compound of formula LXIII as the starting material:

STEP 1D

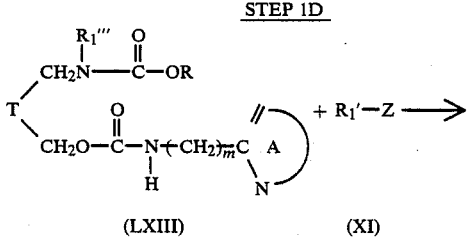

(LXIII)     (XI)

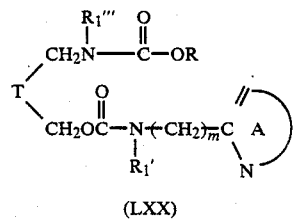

(LXX)

where R, T, $R_1'''$, m, A, $R_1'$ and Z are as defined above.

STEP 2D

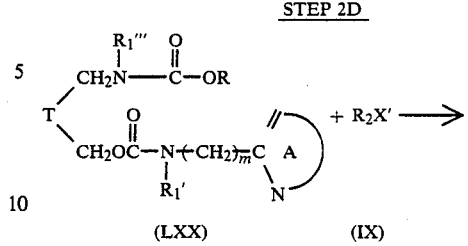

(LXX)     (IX)

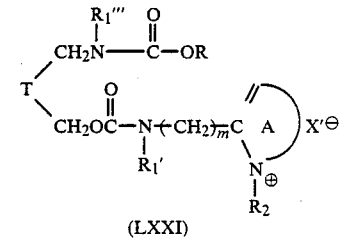

(LXXI)

where R, T, $R_1'''$, m, A, $R_1'$, $R_2$ and X" are as defined above.

With respect to the reaction conditions involving Steps 1D and 2D for preparing a compound of formulae LXX and LXXI, respectively, they are essentially identical to that described above in Steps A and B.

Moreover, the corresponding chloride salt of a compound of formula LXXI may be prepared by the exchange reaction described above for preparing a chloride salt of a compound of formula X.

When a compound of formula I is desired where Y is

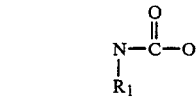

where $R_1$ is other than hydrogen or $C_1$–$C_4$ alkyl, the other $R_1$ is $C_1$–$C_4$ alkyl, $X^\ominus$ is bromide, iodide or $C_1$–$C_4$-alkylsulfonate, and T, R, m, A and $R_2$ are as defined above, it has been found more desirable to employ a three-step reaction employing a compound of formula LXI as the starting material. By reacting said compound with the compound of formula XIV as described above in Step 1, and utilizing a compound so produced in carrying out the reactions described above in Steps 2 and 3, results in a compound having the formula

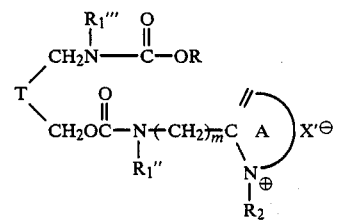

The compounds of formula I where Y is

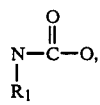

where $R_1$ is $C_1$-$C_4$ alkyl, the other $R_1$ is other than hydrogen, $X^\ominus$ is bromide, iodide or $C_1$-$C_4$ alkylsulfonate, and T, R, m, A and $R_2$ are as defined above may be prepared as illustrated below employing a compound of formula LXVIII as the starting material:

REACTION 1D

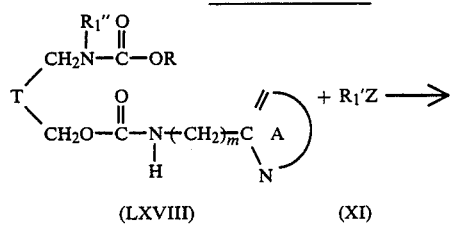

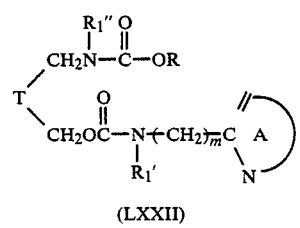

where R, T, $R_1''$, m, A, $R_1'$ and Z are as defined above.

REACTION 2D

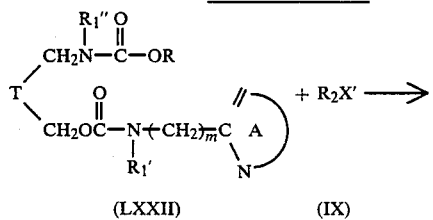

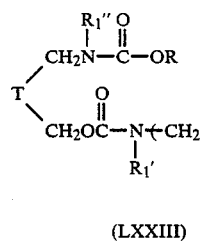

where R, T, $R_1''$, m, A, $R_1'$, $R_2$ and X' are as defined above.

As regards to the reaction conditions concerning Reactions 1D and 2D for preparing a compound of formulae LXXII and LXXIII, respectively, they are analogous to that described above in Steps A and B.

Moreover, the corresponding chloride salt of a compound of formula LXXIII may be prepared by the exchange reaction described above for preparing a chloride salt of a compound of formula X.

When a compound of formula I is desired where Y is

where $R_1$ is $C_1$-$C_4$ alkyl, the other $R_1$ is $C_1$-$C_4$-alkyl, $X^\ominus$ is bromide, iodide or $C_1$-$C_4$ alkylsulfonate, and T, R, m, A and $R_2$ are as defined above, it has been found more desirable to employ a three-step reaction employing a compound of formula LXVI as the starting material. By reacting said compound with the compound of formula XIV as described above in Step 1, and utilizing a compound so produced in carrying out the reactions described above in Steps 2 and 3, results in a compound having the formula

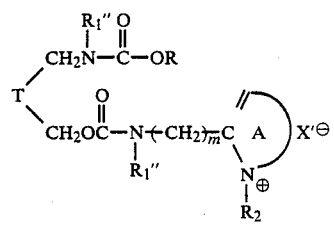

It should be understood that when any of the previously described processes involve the preparation of compounds where R is a functionality sensitive to hydrogenolysis, i.e., alkenyl or alkynyl, the debenzylation should be effected employing a trialkylsilyliodide compound. For example, in the preparation of compounds of Formula I where Y is

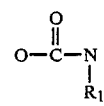

where $R_1$ is other than hydrogen or $C_1$-$C_4$-alkyl, the other $R_1$ is hydrogen, $X^\ominus$ is bromide, iodide or $C_1$-$C_4$ alkylsulfonate, and T, m, A and $R_2$ are as defined above, the debenzylation step may be conducted as depicted below:

STEP 4A-A

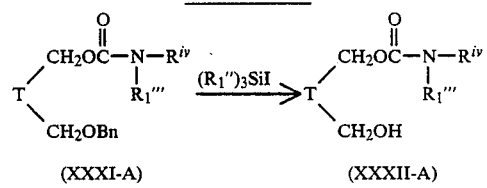

where $R^{IV}$ is n-$C_{12}$-$C_{20}$ alkenyl or alkynyl, and $R_1'''$, $R_1''$ and Bn are as defined above.

As to the reaction conditions. Step 4A—A involves the reaction of a compound of formula XXXI-A with a trialkylsilyliodide compound, preferably trimethylsilyliodide, to yield a compound of formula XXXII-A. The reaction is optionally conducted in the presence of a cosolvent, e.g., an aromatic hydrocarbon such as benzene or toluene, or a lower alkyl nitrile such as acetonitrile, at a temperature of from 20° to 110° C. for a period of between 1 and 24 hours.

As to any of the particular starting materials set forth above, e.g., the compounds of formulae II, III, V, VII, IX, XI, etc., they are either known and obtained by methods described in the literature or, where not known, may be obtained by methods analogous to those described in the literature.

The product of each reaction may, if desired, be purified by conventional techniques such as recrystallization (if a solid), column chromatography, preparative thin layer chromatography, gas chromatography (if sufficiently volatile), or fractional distillation under high vacuum (if sufficiently volatile). Often, however, the crude product of one reaction may be employed in the following reaction without purification.

As is evident to those skilled in the art, all of the compounds of formula I can exist as stereoisomers and such stereoisomers and their enantiomers are contemplated as being included within the scope of this invention.

All of the compounds of formula I are useful as platelet activating factor inhibitors as indicated by their ability to inhibit platelet activating factor (PAF)-induced human platelet aggregation in vitro according to the Platelet Aggregation Inhibition Assay test (PAIA test) as follows:

Human subjects are kept aspirin free for one week and fasted overnight. Platelet rich plasma (PRP) is prepared by centrifugation (200×g.) of freshly drawn blood anti-coagulated with 0.38% sodium citrate (final concentration). Platelet count is adjusted to 250,000 per $\mu$l using platelet poor plasma (PPP) obtained by a second centrifugation (700×g.) of the blood sample. An aliquot (0.38 ml) of the PRP is dispensed into cuvettes and maintained at room temperature (22° C.) until used (but for not more than two hours). The PRP-containing cuvettes are incubated at 37° C. and stirred at 900 rpm within a Payton Aggregometer which is activated to follow the light deflection pattern prior to the addition of the test compound. The test compound (dissolved in a suitable solvent mixture which does not influence platelet aggregation) is then added to a PRP-containing cuvette in an amount sufficient to provide a final concentration of 100 $\mu$M. Between one and two minutes after the addition of the test compound, and aggregation inducing agent (C-16 RAF-Sandoz-Hanover), dissolved in a buffer consisting of 0.01M Tris-Tyrodes buffer with 0.25% bovine serum albumin (pH 7.4), is added to the PRP-containing cuvettes in an amount predetermined to give a consistent aggregation response (either 0.1 $\mu$M or 0.01 $\mu$M). All aggregations are allowed to proceed for 6 minutes for the addition of the inducing agent. The aggregation response is quantitated by determining the area under the curve (AUC). The AUC calculated for the inducing agent alone is considered to be one hundred percent. The potential percent inhibition of the aggregation response is determined by dividing the AUC generated in the presence of the compound by the AUC of the inducing agent alone, multiplying by 100 and then subtracting from 100. The compounds demonstrating greater than 50% inhibition at 100 $\mu$M are evaluated at lower concentrations to generate an IC$_{50}$ (50% inhibitory concentration) value.

Moreover, it has been found that all of the compounds of formula I are useful as platelet activating factor receptor antagonists as indicated by their ability to inhibit specific binding of [$^3$H]-PAF to platelets according to the Human Platelet PAF Receptor Assay test (Test A) as follows:

Human blood is obtained by venipuncture of healthy, human donors into an anti-coagulant mixture containing 3.15% of trisodium citrate and 20 $\mu$g/ml of Prostaglandin I$_2$ (PGI$_2$) in a ratio of blood to anti-coagulant of 9:1. Platelet rich plasma (PRP) is prepared by centrifugation (250×g) of the blood for 20 minutes at room temperature. The PRP is then centrifuged (900×g) for 10 minutes at room temperature and the platelet pellet is washed two times with Tris-Tyrode's (TT) solution having a pH of 7.4 and containing 0.25% bovine serum albumin (BSA), and to which has been added PGI$_2$ at a final concentration of 0.3 g/ml. The platelets are resuspended at 350,000 $\mu$l in TT/BSA containing 1.4 mM CaCl$_2$.2H$_2$O and 0.7 mM MgCl$_2$.6H$_2$O. All of the tests are conducted in duplicate and each of the test compounds is evaluated at concentrations of 100, 50, 1 and 0.1 $\mu$M. For each determination, the following solutions are mixed:

500 $\mu$l of the above-described platelets;
10 $\mu$l of [$^3$H]-PAF (40,000 counts per minute (cpm) to a final concentration of 1.5 $\mu$M); and either
10 $\mu$l of the test compound at 50× the desired final concentration,
10 $\mu$l of vehicle (total bound), or
10 $\mu$l of 1.85×10$^{-5}$M cold PAF (non-specifically bound), Each mixture is allowed to incubate at room temperature for one hour, after which time the reaction is terminated by the addition of 500 $\mu$l of ice cold TT/BSA and centrifugation (900×g) at 4° C., for 10 minutes. The resultant supernatant is aspirated into scintillation vials and the pellet is washed with 250 ml. of ice cold TT/BSA and centrifuged (900×g) at 4° C., for 10 minutes. The supernatants are then aspirated into the same scintillation vials as before and 10 ml, of Scintiverse II (a liquid scintillation cocktail) is added to and mixed therewith. The pellets are resuspended in 500 $\mu$l of Scintiverse II and mixed well. An additional 2 ml, of Scintiverse II is then added to the vials and, after mixing, the vials are counted for 1 minute in a liquid scintillation spectrometer. The amount of specific binding is calculated as the difference in cpm between the total bound [$^3$H]-PAF and non-specifically bound [$^3$H]-PAF. The percent inhibition of specific binding is determined by dividing the cpm specifically bound in the presence of the test compound by the cpm specifically bound in total, multiplying by 100 and then subtracting from 100. An IC$_{50}$ (50% inhibitory concentration) value is generated by evaluating the test compound over the full concentration range.

Furthermore, in view of their usefulness as PAF receptor antagonists, the compounds of formula I have been found useful as inhibitors of PAF-mediated broncho-constriction, which property was evaluated by the PAF-induced Pulmonary Inflation Pressure (PIP) Increase test (Test B) as follows:

Male guinea pigs, weighing between 300 and 400 gm, are anesthetized, after which time trachea tube, carotid and jugular catheters are inserted. The test animal is then force ventilated employing a small animal Harvard respirator and the resistance to lung inflation (PIP) is measured utilizing a pressure transducer and recorder. The test compound is administered orally at 30 minutes prior to, intravenously (jugular) at 5 minutes prior to, or intraarterially at 1 to 5 minutes prior to the introduction of PAF. The PAF (C$_{18}$-Sandoz, Hanover) is dissolved in Tris-Tyrode's bovine serum albumin buffer and administered intravenously (jugular) at 100 ng/kg. Any blood pressure measurements taken are recorded from a transducer attached to the carotid catheter. Two responses are noted in the PIP recordings after the PAF is administered: (1) an immediate response which, in PAF-only treated test animals, averages out to between 70% and 80% more than the baseline PIP values. (This early response is also the greatest response and is, therefore, termed mazimal PIP); and (2) the long term (at least 30 minutes) PIP response which slowly decreases to baseline. A reading at 15 minutes after the administration of PAF is termed the endpoint PIP. The effect of the test compound on the PIP response is determined by the difference between the percent increase in maximal PIP over baseline for the test animal to which has been administered PAF and the test compound compared to the test animal to which only PAF has been administered to generate an ED 50 (dose needed to effect a 50% response).

Still further, the compounds of formula I are useful as inhibitors of PAF-mediated extravasation (the extrusion of plasma from the lumen of the blood vessels into the vessel wall and surrounding tissues) measured as a function of hemoconcentration according to the PAF-induced Extravasation test (Test C) as follows:

Male guinea pigs, weighing between 300 and 400 gm, are anesthetized, after which time a femoral catheter is inserted. The test compound is administered intraarterially at one to five minutes prior to the introduction of PAF. The PAF ($C_{18}$-Sandoz, Hanover) is dissolved in Tris-Tyrode's bovine serum albumin buffer and administered intravenously (jugular) at 100 ng/kg.

To determine the hematocrit value, which is employed to index hemoconcentration and is defined as the percent of packed red blood cells in a sample of blood which is centrifuged to separate plasma from the cellular components, blood samples are collected in 50 $\mu$l heparinized hematocrit tubes. These samples are taken just prior to the injection of PAF, one minute subsequent to the injection of PAF and every two minutes thereafter until 15 minutes has lapsed subsequent to the injection of PAF. The tubes are then centrifuged and the percent of packed red blood cells (hematocrit) is measured (PAF induces a maximal increase in hematocrit at 5 to 7 minutes subsequent to the injection of PAF). The percent increase in hematocrit over the value prior to the injection of PAF is calculated. The hematocrit values obtained with the test compound are compared to the hemoconcentration values obtained with PAF alone and are expressed as percent inhibition of percent increase in hematocrit. From the values obtained, an $ED_{50}$ is generated.

Yet still further, the compounds of formula I are useful as inhibitors of PAF-induced hypotension as measured by their ability to inhibit the lowering of blood pressure levels induced by PAF according to the following test (Test D):

Male Wistar rats, weighing approximately 300 gm, are anesthetized and their carotid arteries cannulated to enable their diastolic and systolic arterial blood pressure measurements to be recorded. PAF is then administered intravenously at either 100 or 500 ng/kg, and the blood pressure drop (within 10 sec.) and recovery time required to reach the pre-injection blood pressure level are measured. At 100 ng/kg, a 30% decrease in blood pressure and a 3 to 4 minute recovery time are observed, whereas at 500 ng/kg, a 52% decrease in blood pressure and a 10 minute recovery time are observed. In order to measure the effectiveness of a compound for both the inhibition of blood pressure decreases and shortening of the recovery time, the test compound is administered intravenously over a range of between 5 and 7 dosage levels (1 or 2 test animals per dose) and between 1 and 5 minutes prior to the introduction of PAF to generate an $ED_{50}$.

Yet even still further, the compounds of formula I are useful as inhibitors of PAF-induced ischemic intestinal necrosis, which property was measured in accordance with the following test (Test E):

Following essentially the procedure of F. Gonzalez-Crussi and W. Hsueh published in J. Amer. Pathol., 112, pgs. 127–135 (1983), male Sprague-Dawley rats, weighing approximately between 260 and 300 g, are anesthetized and their carotid arteries cannulated and connected to a blood pressure transducer and recorder. The test compound is introduced into a cannula inserted into the jugular vein at a time 10 minutes prior to the administration of PAF. The abdomen is then incised along the midline and 2 $\mu$g of PAF or 20 $\mu$g of LPS (lipopolysaccharide) immediately followed by 1 $\mu$g of PAF are injected into the abdominal aorta at the level of the renal artery. The abdominal incision is then covered with saline-moistened gauze and the intestine exposed and examined periodically up to 2 to 3 hours prior to sacrifice. Into the jugular vein is then injected 5 ml of 2% Evans Blue to assess the degree of intestinal perfusion. Blocks of intestinal tissue are then taken for microscopic examination to determine either the extent of necrosis or to verify the absence of necrosis when inhibited by the test compound. Microscopic changes in the intestine are assessed by hematoxylin and eosin staining. The test compound is assessed for its ability to alleviate or prevent the development of gross and microscopic lesions and may be expressed in terms of the number of animals in which inhibition is observed relative to the control (taken to be 100%).

Yet even more still further, the compounds of formula I are useful as inhibitors of PAF-mediated, endotoxin-induced lung injury and, analogously, endotoxin-induced-septic shock and adult respiratory distress syndrome. The ability of the compounds of formula I to inhibit PAF-mediated, endotoxin-induced lung injury can be measured in accordance with the test presented by S. Chang at the 2nd International Conference on *Platelet Activating, Factor and Structurally Related Alkyl Ether Lipids* in Gatlinburg, Tennessee on Oct. 26–29, 1986.

Based on previous reports that lung tissue and blood PAF increased in endotoxin-treated rats, it was determined that the intraperitoneal administration of 2 mg/kg of endotoxin (*S. enteritidis*) causes acute lung injury, as assessed by the extravascular accumulation of water and $^{125}$I-albumin in perfused lungs isolated from rats ninety minutes following in vivo endotoxin treatment. Thus, the wet lung/body weight ratio (as an index of lung water content) increases from 5.35±0.48 to 8.26±0.36 and the albumin leak index increases from 0.46±0.09 to 1.01±0.07.

In order to measure the effectiveness of a compound as an inhibitor of endotoxin-induced lung injury, the test compound is administered intraperitoneally prior to the in vivo endotoxin treatment.

The ability of the compounds of formula I to inhibit PAF-mediated, endotoxin-induced septic shock can be measured in accordance with the test presented by C. N. Sessler, et al at the Annual Meeting of the American Federation for Clinical Research in New Orleans, La. during January, 1987.

All sheep are prepared for testing employing the Chronic Sheep Lung Lymph preparation which is well documented in the literature, with the modifications that chronic tracheostomies are performed on the test animals and pleural pressure catheters inserted at the time of the initial surgery. All catheters are brought to the outside through stab wounds in the skin, the chest is closed and the test animals are allowed to recover for several days until they appear healthy and lung lymphs are free of blood before experiments are commenced.

In order to measure the effectiveness of a compound as an inhibitor of some of the important hemodynamic effects of endotoxin on septic shock, 1.3 μg/kg of endotoxin or saline is administered to groups of test animals intravenously over a 30 minute period and 20 mg/kg of the test compound or saline is administered intravenously over a five-hour period. The pulmonary arterial pressure (PAP), cardiac output (CO) and partial oxygen pressure ($PO_2$) are monitored continuously over the five-hour period.

The ability of the compounds of formula I to inhibit PAF-mediated, endotoxin-induced adult respiratory distress syndrome can be measured in accordance with the test presented by B. W. Christman, et al at the Annual Meeting of the American Thoracic Society and American Lung Association on May 10th–13th, 1987. (Test H)

In order to measure the effectiveness of a compound as an inhibitor of some of the important hemodynamic effects of endotoxin on adult respiratory distress syndrome, 0.5 ug/kg of *E. coli* endotoxin over a 20 minute period, 20 mg/kg/hr of the test compound for 6 hours, or 0.5 ug/kg of *E. coli* endotoxin 1 hour after commencing 20 mg/kg/hr of the test compound for 6 hours, are administered to groups of test animals intravenously. The pulmonary arterial pressure (PAP), dynamic compliance (DC) of the lungs and lung lymph flow (LLF) are monitored continuously over a five-hour period.

As indicated above, certain of the compounds of formula I, viz., the compounds of formula Ic, are especially useful as PAF inhibitors in that they exhibit a long duration of PAF inhibition, which property can be measured by any of the above-described test procedures, aptly modified in order to determine the decrease in inhibition over time. Thus, a decrease in inhibition of bronchoconstriction over time (Test I) can be measured by a modification of Test B described above wherein an amount of the test compound which is x times the $ED_{50}$ for the compound is intravenously administered to the test animals. By observing the time at which the test compound still inhibits 50% of the bronchoconstriction caused by the PAF challenge, the rate of loss of the test compound can be determined employing the following equation:

$$\text{Rate of loss (ug/kg/min)} = \frac{\text{Dose (mg)} - ED_{50} \text{ (mg)}}{\text{time (in minutes)}},$$

Similarly, a decrease in inhibition of hemoconcentration over time (Test J) can be measured by a modification of Test C described above wherein an amount of the test compound which is x times the $ED_{50}$ for the compound is intravenously administered to the test animals. By observing the time at which the test compound still inhibits 50% of the hemoconcentration caused by the PAF challenge, the rate of loss of the test compound can be determined employing the above equation.

The compounds of formula I may be combined with one or more pharmaceutically acceptable carriers and, optionally, one or more other conventional pharmaceutical adjuvants and administered orally in the form of tablets dispersible powders, granules, capsules, elixirs, suspensions and the like or parenterally in the form of sterile injectable solutions or suspensions. The compositions may be prepared by conventional means.

The precise dosage of a compound of formula I to be employed for inhibiting platelet activating factor (PAF) depends upon several factors including the host, the nature and the severity of the condition being treated, the mode of administration and the particular compound employed. However, in general, satisfactory inhibition or antagonism of platelet activating factor is achieved when a compound of formula I is administered orally at a daily dosage of 0.05–100, preferably 0.1–30 mg/kg body weight or, for most larger primates, a daily dosage of 1–500 mg, preferably 1–50 mg. A typical oral dosage is 5 mg, three times a day.

As with the PAF inhibition use, the precise dosage of a compound of formula I to be employed in treating PAF-mediated bronchoconstriction and extravasation, PAF-induced hypotension, PAF-involved ischemic bowel disease and PAF-mediated, endotoxin-induced lung injury depends upon several factors including the host, the nature and severity of the condition being treated, the mode of administration and the particular compound employed. However, in general, satisfactory inhibition or antagonism of PAF-mediated bronchoconstriction and extravasation, PAF-induced hypotension, PAF-induced ischemic bowel disease and PAF-mediated, endotoxin-induced lung injury is achieved when a compound of formula I is administered orally at a daily dosage of 0.2–100, preferably 0.2–50 mg/kg body weight or, for most larger primates, a daily dosage of 10–2000 mg, preferably 10–350 mg. A typical oral dosage is 50 or 100 mg, two or three times a day.

Regardless of use, a small dosage is gradually increased until the optimal dosage for the host under treatment is determined. For administration by injection, a dosage somewhat lower than would be used for oral administration of the same compound to the same host having the same condition is usually employed.

The compounds of formula I may be formulated into such pharmaceutical compositions containing an amount of the active substance that is effective for inhibiting PAF, in treating PAF-mediated bronchoconstriction and extravasation, in treating PAF-induced hypotension, in treating ischemic bowel disease or in treating PAF-mediated, endotoxin-induced lung injury, such compositions in unit dosage form and such compositions comprising a solid pharmaceutically acceptable carrier.

Tablets and capsules containing the ingredients indicated below may be prepared by conventional techniques and are useful as platelet activating factor inhibitors. The tablet may be administered once or twice a day whereas the capsule is suitably administered three times a day.

| Ingredients | Weight (mg) tablet | capsule |
|---|---|---|
| compound of formula I, e.g. the compound of Example 1 | 5 | 5 |

-continued

| Ingredients | Weight (mg) tablet | capsule |
|---|---|---|
| tragacanth | 10 | — |
| lactose (spray-dried) | 257.5 | 95 |
| cornstarch | 15 | — |
| talcum | 10 | — |
| magnesium stearate | 2.5 | — |
| Total | 300.0 | 100 |

The following are representative of tablets and capsules which may be prepared by conventional means and are useful in treating PAF-mediated bronchoconstriction and extravasation, PAF-induced hypotension, PAF-involved ischemic bowel disease and PAF-mediated, endotoxin-induced lung injury. The tablet and the capsule may be suitably administered two or three times a day.

| Ingredients | Weight (mg) tablet | capsule |
|---|---|---|
| compound of formula I, e.g., the compound of Example 1 | 50 | 50 |
| tragacanth | 10 | — |
| lactose (spray-dried) | 212.5 | 100 |
| cornstarch | 15 | — |
| talcum | 10 | — |
| magnesium stearate | 2.5 | — |
| Total | 300.0 | 150.0 |

The following examples show representative compounds encompassed by this invention and their synthesis. However, it should be clearly understood that they are for purposes of illustration only.

EXAMPLE 1

2-[Acetyl[[tetrahydro-2-[[[[(octadecyl)-amino]carbonyl]oxy]methyl]furan-2-yl]-methoxycarbonyl]aminomethyl]-1-ethylpyridinium chloride

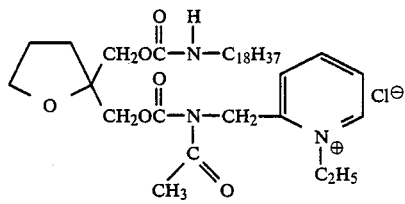

(a) Preparation of 2-[[phenoxy(carbonyl)-oxy]methyl]-2-[[[[(octadecyl)amino]carbonyl]-oxy]methyl]-tetrahydrofuran To a stirred solution of 4.27 g (10 mmol) of 2-hydroxymethyl-2-[[[[(octadecyl)amino]carbonyl]oxy]methyl]-tetrahydrofuran and 1.58 g (20 mmol) of pyridine in 20 ml of methylene chloride, which was cooled in an ice bath, was added, dropwise, 2.03 g (13 mmol) of phenyl chloroformate. The resultant mixture was then allowed to warm to room temperature and, after maintaining this temperature for 24 hours, additional methylene chloride was added. The resultant solution was then washed successively with 3N hydrochloric acid, saturated sodium bicarbonate and water. The organic layer was then dried over anhydrous sodium sulfate, filtered and concentrated to afford the crude product. The crude product was then dissolved in a small amount of hot ether, diluted with petroleum ether and refrigerated. The refrigerated product was then washed with cold ether and petroleum ether and, upon drying, a solid was obtained.

(b) Preparation of 2-[[[[(2-pyridinyl)-methyl]amino]-carbonyl]oxy]methyl]-2-[[[[(octadecyl)amino]carbonyl]oxy]methyl]-tetrahydrofuran To 4.09 g (7.5 mmol) of the compound prepared in (a) above dissolved in 20 ml of chloroform was added, with stirring and under a nitrogen atmosphere 0.97 g (9.0 mmol) of 2-(aminomethyl)pyridine. The resultant mixture was then heated to reflux and maintained at the reflux temperature for 20 hours, after which time it was cooled and concentrated to afford the crude product. The crude product was then chromatographed on silica gel employing, successively as the eluents, a mixture of petroleum ether and ethyl acetate in increasing amounts of the latter, the initial ratio being 80:20 by volume, with elution taking place when the ratio became 30:70 by volume. Upon elution with ethyl acetate and concentrating the eluted product, a solid was obtained.

(c) Preparation of 2-[[[[acetyl-[(2-pyridinyl)methyl]amino]carbonyl]oxy]methyl]-2-[[[[(octadecyl)amino]carbonyl]oxy]methyl]tetrahydrofuran To 3.2 g (5.7 mmol) of the compound prepared in (b) above dissolved in 25 ml of chloroform was added, with stirring and under a nitrogen atmosphere, 18.15 g (180 mmol) of triethylamine, 11.63 g (114 mmol) of acetic anhydride and 0.035 g (0.29 mmol) of 4-dimethylaminopyridine. The resultant mixture was then heated to reflux and maintained at the reflux temperature for 72 hours. The volatiles were then removed under high vacuum and the resultant residue was dissolved in methylene chloride and washed rapidly with a saturated aqueous sodium bicarbonate solution. The organic layer was then dried over sodium sulfate, filtered and concentrated. The resultant residue was then chromatographed on silica gel employing a mixture of petroleum ether and ethyl acetate in a ratio of 1:1 by volume initially, with the product being eluted when the eluent was pure ethyl acetate. The resultant solution was then concentrated to obtain a semi-solid.

Preparation of the title compound (i) To 9.75 g (62.5 mmol) of iodoethane was added, with stirring and under a nitrogen atmosphere, 0.90 g (1.5 mmol) of the compound prepared in (c) above. The resultant mixture was then warmed to reflux and maintained at this temperature for 72 hours, with an additional 19.5 g (125 mmol) of iodoethane added after 20 hours. At the end of 72 hours, the excess iodoethane was removed at reduced pressure and the residue was washed with a mixture of ether and ethyl acetate.

(ii) Exchange of chloride ion for the iodide ion

The resultant residue from (i) above was dissolved in methanol and passed rapidly through a prewashed IRA-410 (Cl$^{\ominus}$) column. The solvent was then removed under vacuum and the residue was chromatographed on silica gel employing, successively as the eluents, a mixture of methylene chloride and methanol in an initial ratio of 90:10 by volume, with elution taking place when the ratio became 80:20 by volume. The eluted product was then concentrated to yield the title compound as a white solid.

PAIA test—IC$_{50}$—0.04 μM
Test A—IC$_{50}$—0.01 μM
Test B—ED$_{50}$—2.5 μg/kg (i.a.)
Test C—ED$_{50}$—2.8 μg/kg (i.a.)
Test D—ED$_{50}$—3 μg/kg (i.v.)
Test I—Rate of loss=0.3 μg/kg/min.

Test J—Rate of loss=0.35 μg/kg/min.

EXAMPLE 2

2-[[[Tetrahydro-2-[[[[(octadecyl)amino]carbonyl]oxy]-methyl]furan-2-yl]methoxycarbonyl]aminomethyl]-1-ethylpyridinium chloride

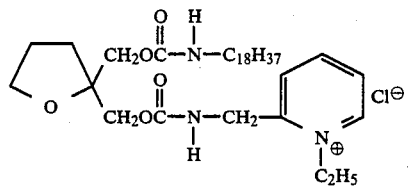

The resultant residue from (i) in the last step of the procedure for preparing the compound of Example 1 was dissolved in a mixture of methanol and water in a 9:1 ratio by volume and passed through an IRA-410 (Cl⊖) column. The solvent was then removed under vacuum and the residue was chromatographed on silica gel employing, successively as the eluents, a mixture of methylene chloride and methanol in an initial ratio of 90:10 by volume, with elution taking place when the ratio became 80:20 by volume. The eluted product was then concentrated to yield the title compound.

PAIA test—$IC_{50}$—16 μM
Test A—$IC_{50}$—0.80 μM

EXAMPLE 3

2-[5-[[[Tetrahydro-2-[[[[(octadecyl)-amino]carbonyl]oxy]methyl]furan-2-yl]methoxycarbonyl]amino]pentyl]-1-ethylpyridinium chloride

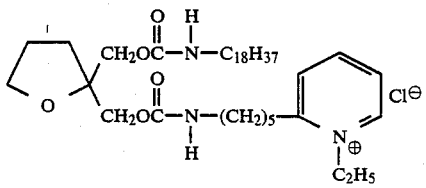

(a) Preparation of 2-[[[[[5-(2-pyridinyl)pentyl]amino]-carbonyl]oxy]methyl]-2-[[[[(octadecyl)amino]carbonyl]oxy]methyl]tetrahydrofuran Following essentially the procedure of Example 1(b), and using in place of 2-(aminomethyl)pyridine, an approximately equivalent amount of 2-(5-aminopentyl)-pyridine, a white solid was obtained.

Preparation of the title compound (i) To 2.16 g (14 mmol) of iodoethane was added, with stirring and under a nitrogen atmosphere, 0.206 g (0.33 mmol) of the compound prepared in (a) above. The resultant mixture was then warmed to reflux, maintained at this temperature for 24 hours, and the excess iodoethane was removed at reduced pressure.

(ii) Exchange of chloride ion for the iodide ion

The resultant residue from (i) above was dissolved in a mixture of methanol and water in a 9:1 ratio by volume and passed rapidly through a prewashed IRA-410 (Cl⊖) column. The solvent was then removed under vacuum and the residue was chromatographed on silica gel employing successively as the eluents, a mixture of methylene chloride and methanol in an initial ratio of 90:10 by volume, with elution taking place when the ratio became 80:20 by volume. The eluted product was then concentrated to yield the title compound as a white solid.

PAIA test—$IC_{50}$—0.3 μM
Test A—$IC_{50}$—0.02 μM
Test B—$ED_{50}$—5.0 μg/kg (i.a.)
Test C—$ED_{50}$—8.5 μg/kg (i.a.)
Test D—$ED_{50}$—27 μg/kg (i.v.)
Test I—Rate of loss=0.66 μg/kg/min.
Test J—Rate of loss=0.65 μg/kg/min.

EXAMPLE 4

2-[5-[Acetyl[[tetrahydro-2-[[[[(octadecyl)-amino]carbonyl]oxy]methyl]furan-2-yl]methoxycarbonyl]amino]-pentyl]-1-ethylpyridinium chloride

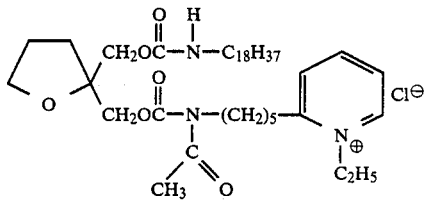

(a) Preparation of 2-[[[[acetyl[5-(2-pyridinyl)pentyl]amino]carbonyl]oxy]methyl]-2-[[[[(octadecyl)amino]-carbonyl]oxy]methyl]tetrahydrofuran To 1 ml of a 12.5% solution of phosgene in toluene was added, with stirring, a solution of 0.21 g (0.5 mmol) of 2-hydroxymethyl-2-[[[[(octadecyl)amino]-carbonyl]oxy]methyl]tetrahydrofuran, 0.10 g (0.5 mmol) of 2-(5-acetamidopentyl)pyridine, and 0.101 g (1.0 mmol) of triethylamine in toluene. The resultant mixture was then allowed to react for 2 hours, after which time an additional 0.42 g (1.0 mmol) of the tetrahydrofuran compound was added and the mixture allowed to react, with stirring, for 24 hours. The reaction mixture was then diluted with ethyl acetate and washed with water. The organic solution was then dried and concentrated to afford a crude residue which was acetylated with 0.20 g (2 mmol) of acetic anhydride in 0.50 g (5 mmol) of pyridine to form the acetate of the excess tetrahydrofuran compound to allow for easier separation of this starting material from the desired end product. The volatiles were then removed and the residue chromatographed on silica gel employing, successively as the eluents, a mixture of petroleum ether and ethyl acetate in increasing amounts of the latter, the initial ratio being 6:4 by volume, with elution taking place when the ratio became 4:6 by volume. The eluted product was then concentrated to yield a solid.

Preparation of the title compound (i) To 9.75 g (62.5 mmol) of iodoethane was added, with stirring and under a nitrogen atmosphere, 0.043 g (0.065 mmol) of the compound prepared in (a) above. The resultant mixture was then warmed to reflux, maintained at this temperature for 24 hours, and the excess iodoethane was removed at reduced pressure.

(ii) Exchange of chloride ion for the iodide ion

The resultant residue from (i) above was dissolved in a mixture of methanol and water in a 9:1 ratio by volume and passed rapidly through a prewashed IRA-410 (Cl⊖) column. The solvent was then removed under vacuum and the residue was chromatographed on silica gel employing, successively as the eluents, a mixture of methylene chloride and methanol in an initial ratio of 90:10 by volume, with elution taking place when the ratio became 85:15 by volume. The eluted product was then concentrated to yield the title compound as a white solid.

PAIA test—IC$_{50}$—0.13 μM
Test A—IC$_{50}$—0.008 μM
Test B—ED$_{50}$—15 μg/kg (i.a.)
Test C—ED$_{50}$—17 μg/kg (i.a.)
Test I—Rate of loss=0.35 μg/kg/min.
Test J—Rate of loss=1.10 μg/kg/min.

EXAMPLE 5

2-[Acetyl[[tetrahydro-2-[[[[[acetyl(octadecyl)amino]-carbonyl]oxy]methyl]furan-2-yl]methoxycarbonyl-]aminomethyl]-1-ethylpyridinium chloride.

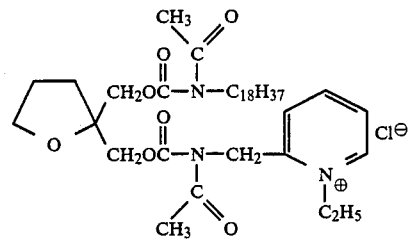

(a) Preparation of 2-[[[[acetyl[(2-pyridinyl)methyl-]amino]carbonyl]oxy]methyl]-2-[[[[[acetyl](octadecyl-)amino]carbonyl]oxy]-methyl]tetrahydrofuran To 0.070 g (0.125 mmol) of the compound prepared in Example 1(b) dissolved in 1 ml of dry chloroform was added, with stirring and under a nitrogen atmosphere, 0.098 g (1.25 mmol) of acetyl chloride. After stirring the mixture for 60 hours at room temperature, 0.151 g (1.51 mmol) of triethylamine was added and the resultant mixture was warmed to 80° C. and maintained at this temperature for 24 hours. The volatiles were then removed under high vacuum and the residue was dissolved in methylene chloride and washed rapidly with a saturated aqueous solution of sodium bicarbonate. The organic acid was then dried over sodium sulfate, filtered and concentrated to afford a residue which was chromatographed on silica gel employing a mixture of petroleum ether and ethyl acetate in a ratio of 1:1 by volume initially, with the product being eluted when the eluent was pure ethyl acetate. The resultant solution was then concentrated to obtain a solid.

Preparation of the title compound (i) Following essentially part (i) in the last step of the procedure for preparing the compound of Example 4, and using in place of the compound prepared in part (a) of Example 4, an approximately equivalent amount of the compound prepared in (a) above, and instead of maintaining the reflux temperature for 24 hours, it was maintained for 72 hours, the crude iodide compound was obtained.

(ii) Exchange of chloride ion for the iodide ion

Following essentially part (ii) in the last step of the procedure for preparing the compound of Example 1, and using in place of the compound prepared in part (i) of Example 1, an approximately equivalent amount of the compound prepared in (i) above, the title compound was obtained as a white solid.

PAIA test—IC$_{50}$—0.048 μM
Test A—IC$_{50}$—0.002 μM
Test B—ED$_{50}$—4 μg/kg (i.a.)
Test C—ED$_{50}$—4 μg/kg (i.a.)
Test D—ED$_{50}$—4.5 μg/kg (i.v.)

EXAMPLE 6

2-[Trimethylacetyl[[tetrahydro-2-[[[[(octadecyl-)amino]carbonyl]oxy]methyl]furan-2-yl]methoxycarbonyl]aminomethyl]-1-ethylpyridinium chloride

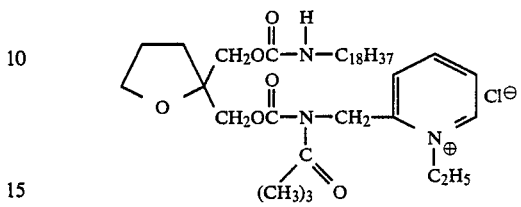

(a) Preparation of 2-[[[[trimethylacetyl-[(2-pyridinyl)-methyl]amino]carbonyl]oxy]methyl]-2-[[[[(octadecyl-)amino]carbonyl]oxy]methyl]tetrahydrofuran To 0.140 g (0.25 mmol) of the compound prepared in Example 1(b) dissolved in 2 ml of dry chloroform was added, with stirring and under a nitrogen atmosphere, 0.151 g (1.25 mmol) of trimethylacetylchloride. The mixture was stirred for 16 hours at room temperature and then warmed to and maintained at reflux temperature. After 3 hours, 0.036 g (0.36 mmol) of triethylamine was added and the resultant mixture was allowed to react, with stirring, for 20 hours. The volatiles were then removed under high vacuum and the residue was dissolved in methylene chloride and washed rapidly with a saturated aqueous solution of sodium bicarbonate. The organic layer was then dried over sodium sulfate, filtered and concentrated to afford a residue which was chromatographed on silica gel employing a mixture of petroleum ether and ethyl acetate in a ratio of 1:1 by volume initially, with the product being eluted when the eluent was pure ethyl acetate. The resultant solution was then concentrated to obtain a solid.

Preparation of the title compound (i) Following essentially part (i) in the last step of the procedure for preparing the compound of Example 4, and using in place of the compound prepared in part (a) of Example 4, an approximately equivalent amount of the compound prepared in (a) above, the crude iodide compound was obtained.

(ii) Exchange of chloride ion for the iodide ion

Following essentially part (ii) in the last step of the procedure for preparing the compound of Example 1, and using in place of the compound prepared in part (i) of Example 1, an approximately equivalent amount of the compound prepared in (i) above, and conducting the silica gel chromatography employing, successively as the eluents, ethyl acetate and then a mixture of methylene chloride and methanol in an initial ratio of 90:10 by volume, with elution taking place when the ratio became 80:20 by volume, the title compound was obtained as a solid.

PAIA test—IC$_{50}$—0.5 μM
TEST A—IC$_{50}$—0.085 μM

EXAMPLE 7

2-[Benzoyl[[tetrahydro-2-[[[[(octadecyl)amino]carbonyl]oxy]methyl]furan-2-yl]-methoxycarbonyl]aminomethyl]-1-ethylpyridinium chloride

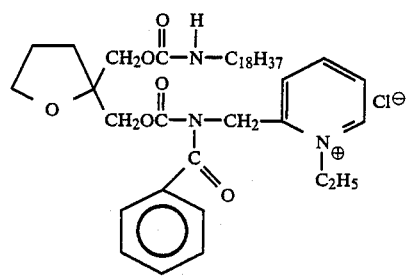

(a) Preparation of 2-[[[[benzoyl-[(2-pyridinyl)methyl]amino]carbonyl]oxy]methyl]-2-[[[[(octadecyl)amino]carbonyl]oxy]methyl]tetrahydrofuran To 0.140 g (0.25 mmol) of the compound prepared in Example 1(b) dissolved in 2.5 ml of dry chloroform was added, with stirring and under a nitrogen atmosphere, 0.176 g (1.25 mmol) of benzoyl chloride. The mixture was stirred for 24 hours at room temperature. The volatiles were then removed under high vacuum and the residue was chromatographed on silica gel employing a mixture of petroleum ether and ethyl acetate as the eluent in a ratio of 1:1 by volume. The resultant solution was then concentrated to obtain a solid.

Preparation of the title compound (i) To 3.9 g (25 mmol) of iodoethane was added, with stirring and under a nitrogen atmosphere, 0.16 g (0.24 mmol) of the compound prepared in (a) above. The resultant mixture was then warmed to reflux and maintained at this temperature for 43 hours. The excess iodoethane was then removed at reduced pressure and the residue was triturated with a mixture of ether and ethyl acetate and then with petroleum ether.

(ii) Exchange of chloride ion for the iodide ion

Following essentially part (ii) in the last step of the procedure for preparing the compound of Example 1, and using in place of the compound prepared in part (i) of Example 1, an approximately equivalent amount of the compound prepared in (i) above, and conducting the silica gel chromatography employing, as the eluent, a mixture of methylene chloride and methanol in a ratio of 80:20 by volume, the title compound was obtained as a solid.

PAIA test—IC$_{50}$—0.84 μM
TEST A—IC$_{50}$—0.016 μM

EXAMPLE 8

2-[Acetyl[[tetrahydro-2-[(octadecyloxy)methyl]furan-2-yl]methoxycarbonyl]aminomethyl]-1-ethylpyridinium chloride

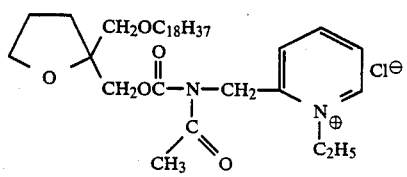

(a) Preparation of 2-[[phenoxy[carbonyl]oxy]methyl]-2-[(octadecyloxy)methyl]tetrahydrofuran Following essentially the procedure of Example 1(a), and using in place of 2-hydroxymethyl-2-[[[[(octadecyl)amino]carbonyl]oxy]methyl]tetrahydrofuran, an approximately equivalent amount of 2-hydroxymethyl-2-[[(octadecyl)oxy]methyl]tetrahydrofuran, an oil was obtained.

(b) Preparation of 2-[[[[[(2-pyridinyl)methyl]amino]carbonyl]oxy]methyl]-2-[(octadecyloxy)-methyl]tetrahydrofuran Following essentially the procedure of Example 1(b), and using in place of the compound prepared in Example 1(a), an approximately equivalent amount of the compound prepared in (a) above, and conducting the silica gel chromatography employing, successively as the eluents, a mixture of petroleum ether and ethyl acetate in increasing amounts of the latter, the initial ratio being 90:10 by volume, with elution taking place when the ratio became 20:80 by volume, concentration of the resultant solution afforded a waxy solid.

(c) Preparation of 2-[[[acetyl[(2-pyridinyl)methyl]amino]carbonyl]oxy]methyl]-2-[(octadecyloxy)methyl]tetrahydrofuran To 0.259 g (0.5 mmol) of the compound prepared in (b) above dissolved in 3 ml of chloroform was added, with stirring and under a nitrogen atmosphere, 0.393 g (5.0 mmol) of acetyl chloride. The resultant mixture was cooled in an ice bath and to the cooled mixture was added, dropwise, 0.51 g (5.0 mmol) of triethylamine. The resultant solution was then warmed to reflux and maintained at the reflux temperature for 2 hours. The volatiles were then removed under high vacuum and the resultant residue was dissolved in methylene chloride and washed rapidly with a saturated aqueous sodium bicarbonate solution. The organic layer was then dried over sodium sulfate, filtered and concentrated. The resultant residue was then chromatographed on silica gel employing, successively as the eluents, a mixture of petroleum ether and ethyl acetate in a ratio of 4:1 by volume initially, with the product being eluted when the eluent was at a ratio of 7:3 by volume. The resultant solution was then concentrated to yield an oil.

Preparation of the title compound (i) Following essentially part (i) in the last step of the procedure for preparing the compound of Example 4, and using in place of the compound prepared in part (a) of Example 4, an approximately equivalent amount of the compound prepared in (c) above, and after maintaining the reflux temperature for 72 hours, the excess iodoethane was removed at reduced pressure to afford the crude iodide compound.

(ii) Exchange of chloride ion for the iodide ion

Following essentially part (ii) in the last step of the procedure for preparing the compound of Example 1, and using in place of the compound prepared in part (i) of Example 1, an approximately equivalent amount of the compound prepared in (i) above, and conducting the silica gel chromatography employing, successively as the eluents, a mixture of methylene chloride and methanol in a ratio of 90:10 by volume initially, with the product being eluted when the eluent was at a ratio of 80:20 by volume, concentration of the eluted product yielded the title compound as a tan waxy solid.

PAIA test—IC$_{50}$—0.86 μM
TEST A—IC$_{50}$—0.014 μM

EXAMPLE 9

Cis-2-[acetyl[[tetrahydro-2,5-dimethyl-5-[[[[(octadecyl-)amino]carbonyl]oxy]methyl]furan-2-yl]methoxycarbonyl]aminomethyl]-1-ethylpyridinium chloride

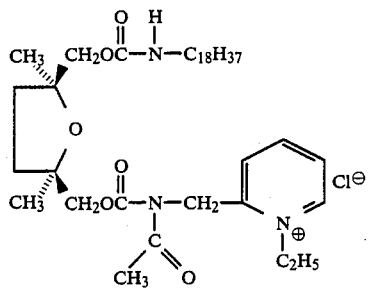

(a) Preparation of 2-[[[phenoxy(carbonyl)oxy]methyl-5-[[[[(octadecyl)amino]carbonyl]oxy]methyl]-2,5-dimethyltetrahydrofuran Following essentially the procedure of Example 1(a), and using in place of 2-hydroxymethyl-2-[[[[(octadecyl)amino]carbonyl]oxy]methyl]tetrahydrofuran, an approximately equivalent amount of cis-2-hydroxymethyl-5-[[[[(octadecyl)amino]carbonyl]oxy]methyl]-2,5-dimethyltetrahydrofuran, a waxy solid was obtained after the crude product was chromatographed on silica gel employing, as the eluent, a mixture of acetone and hexane in a ratio of 1:4 by volume.

(b) Preparation of cis-2-[[[[[(2-pyridinyl)methyl]amino]carbonyl]oxy]methyl]-5-[[[[(octadecyl)amino]carbonyl]oxy]methyl]-2,5-dimethyltetrahydrofuran Following essentially the procedure of Example 1(b), and using in place of the compound prepared in Example 1(a), an approximately equivalent amount of the compound prepared in (a) above, a waxy solid was obtained after the crude product was chromatographed on silica gel employing, as the eluent, a mixture of acetone and hexane in a ratio of 1:3 by volume.

(c) Preparation of cis-2-[[[[acetyl-[(2-pyridinyl)methyl]amino]carbonyl]oxy]methyl]-5-[[[[(octadecyl)amino]carbonyl]oxy]methyl]-2,5-dimethyltetrahydrofuran Following essentially the procedure of Example 1(c), and using in place of the compound prepared in Example 1(b), an approximately equivalent amount of the compound prepared in (b) above, a waxy solid was obtained after the crude product was chromatographed on silica gel employing, as the eluent, a mixture of ethyl acetate and hexane in a ratio of 6:4 by volume.

Preparation of the title compound (i) Following essentially part (i) in the last step of the procedure for preparing the compound of Example 1, and using in place of the compound prepared in Example 1(c), an approximately equivalent amount of the compound prepared in (c) above, the crude iodide compound was obtained.

(ii) Exchange of chloride ion for the iodide ion

Following essentially part (ii) in the last step of the procedure for preparing the compound of Example 1, and using in place of the compound prepared in part (i) of Example 1, an approximately equivalent amount of the compound prepared in (i) above, and conducting the silica gel chromatography employing, as the eluent, a mixture of methylene chloride and methanol in a 9:1 ratio by volume, the title compound was obtained as a tan solid after the eluted product was concentrated, m.p. 42°–44° C.

PAIA test—$IC_{50}$—0.35 μM
Test A—$IC_{50}$—0.06 μM
Test B—$ED_{50}$—20 μg/kg (i.a.)
Test C—$ED_{50}$—15 μg/kg (i.a.)
Test I—Rate of loss=0.88 μg/kg/min.
Test J—Rate of loss=0.92 μg/kg/min.

EXAMPLE 10

Cis-2-[[[tetrahydro-5-[[[[(octadecyl)amino]carbonyl]oxy]methyl]-2,5-dimethyl-furan-2-yl]methoxycarbonyl]aminomethyl]-1-ethylpyridinium chloride

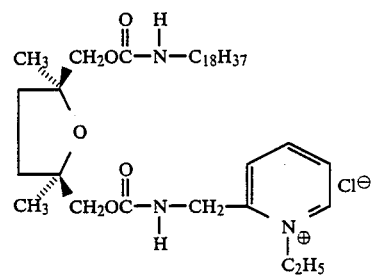

(i) Following essentially part (i) in the last step of the procedure for preparing the compound of Example 1, and using in place the compound prepared in Example 1(c), an approximately equivalent amount of the compound prepared in Example 9(b), the crude iodide compound was obtained.

(ii) Exchange of chloride ion for the iodide ion

Following essentially part (ii) in the last step of the procedure for preparing the compound of Example 1, and using in place of the compound prepared in part (i) of Example 1, an approximately equivalent amount of the compound prepared in (i) above, and conducting the silica gel chromatography employing, as the eluent, a mixture of methylene chloride and methanol in a 17:3 ratio by volume, the title compound was obtained as a white solid after the eluted product was concentrated, m.p. 74°–80° C.

PAIA test—$IC_{50}$—0.55 μM
Test A—$IC_{50}$—0.56 μM
Test B—$ED_{50}$—150 μg/kg (i.a.)
Test C—$ED_{50}$—60 μg/kg (i.a.)
Test I—Rate of loss=30.0 μg/kg/min.
Test J—Rate of loss=10.21 μg/kg/min.

EXAMPLE 11

Cis-2-[[[tetrahydro-2,5-dimethyl-5-[[[[(octadecyl)amino]carbonyl]oxy]methyl]furan-2-yl]methoxycarbonyl]aminomethyl]-1,4,6-trimethylpyridinium chloride

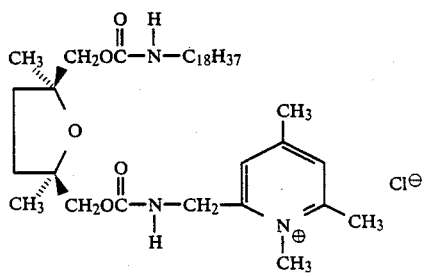

(a) Preparation of cis-2-[[(chlorocarbonyl)oxy]methyl]-5-[[[[(octadecyl)amino]carbonyl]oxy]methyl]2,5-dimethyltetrahydrofuran To an ice cooled, stirred solution of 2.0 g (4.4 mmol) of cis-2-hydroxymethyl-5-[[[[(octadecyl)amino]carbonyl]oxy]methyl]-2,5-dimethyltetrahydrofuran in 25 ml of toluene in a efficient hood was added, dropwise over a period of 2 minutes, 12 ml of 12.5% solution of phosgene in toluene (~15 mmol of phosgene). The cooled, stirred mixture was then allowed to react for 1 hour, after which time an additional 10 ml of the phosgene solution was added. The resultant cooled, stirred mixture was then allowed to react for 1 hour, after which time it was allowed to warm to room temperature. To remove any excess phogene and the hydrogen chloride generated by the reaction, a vacuum of 200 mm was applied employing an adapter which passed through a dilute aqueous solution of sodium hydroxide to a vacuum source. The volatiles were then removed at 40° C. under reduced pressure to afford the crude product as a white waxy solid. The crude product was then chromatographed on silica gel employing, as the eluent, a mixture of ethyl acetate and hexane in a 3:7 ratio by volume. Concentration of the eluted product yielded soft white crystals.

(b) Preparation of cis-2-[[[[[(4,6-dimethylpyridin-2-yl)methyl]amino]carbonyl]oxy]methyl]-5-[[[[(octadecyl)amino]carbonyl]oxy]methyl]-2,5-dimethyltetrahydrofuran To 1.55 g (3 mmol) of the compound prepared in (a) above dissolved in 15 ml of chloroform was successively added, with stirring and under a nitrogen atmosphere, 1.0 g (12 mmol) of sodium bicarbonate and 0.7 g (5 mmol) of 2-aminomethyl-4,6-dimethylpyridine. The resultant mixture was then warmed to 70° C. and maintained at this temperature for 17 hours. The reaction mixture was then filtered and the volatiles were removed at reduced pressure. The crude residue was then chromatographed twice on silica gel employing, as the eluent in each case, a mixture of methylene chloride and methanol, the first at a ratio of 24:1 by volume and the second at a ratio of 49:1 by volume. The eluted product was then concentrated to afford a yellow syrup.

Preparation of the title compound (i) To 200 mg (0.3 mmol) of the compound prepared in (b) above was added, with stirring, 5.0 ml (~80 mmol) of iodomethane. The mixture was then heated to 40° C. and maintained at this temperature for 24 hours. The excess iodomethane was then removed at reduced pressure to afford the crude iodide compound.

(ii) Exchange of chloride ion for the iodide ion

The crude iodide compound from (i) above was dissolved in methanol and passed rapidly through a prewashed IRA-410 (Cl⊖) column. The solvent was then removed under vacuum and the sticky yellow residue was chromatographed on silica gel employing, as the eluent, methylene chloride alone initially and then successively, a mixture of methylene chloride and methanol in increasing amounts of the latter, with elution taking place when a ratio of 85:15 by volume was reached. The eluted product was then concentrated to yield the title compound as a white solid, m.p. 50°-52° C.

PAIA Test—IC$_{50}$—2.2 μM
Test A—IC$_{50}$—0.45 μM

EXAMPLE 12

Cis-2-[methyl[[tetrahydro-2,5-dimethyl-5-[[[[(octadecyl)amino]carbonyl]oxy]methyl]furan-2-yl]methoxycarbonyl]aminomethyl]-1-methylpyridinium chloride

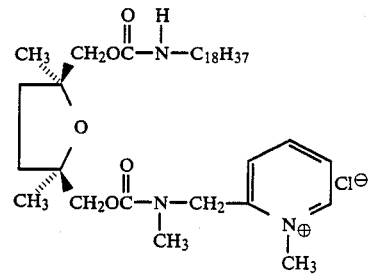

(a) Preparation of cis-2-[[[[[(2-pyridinyl)-methyl]methylamino]carbonyl]oxy]methyl]-5-[[[[(octadecyl)amino]carbonyl]oxy]methyl]-2,5-dimethyltetrahydrofuran To 0.85 g (1.6 mmol) of the compound prepared in Example 11(a) dissolved in 5 ml of chloroform was added, with stirring and under a nitrogen atmosphere, 0.20 g (1.64 mmol) of 2-[(methylamino)methyl]pyridine in 5 ml of chloroform and 0.80 g (9.5 mmol) of sodium bicarbonate. The resultant solution was then warmed to reflux and maintained at the reflux temperature for 3 hours. The solution was then filtered and concentrated at reduced pressure to afford the crude product as an oil. The crude oil was then chromatographed on silica gel employing, as the eluent, a mixture of methylene chloride and methanol in a ratio of 97:3 by volume to yield a colorless viscous oil.

Preparation of the title compound (i) To 300 mg (0.5 mmol) of the compound prepared in (a) above was added, with stirring, 8 ml (~128 mmol) of iodomethane and the mixture was allowed to react at room temperature, with stirring, for 96 hours. The excess iodomethane was then removed at reduced pressure to afford the crude iodide compound.

(ii) Exchange of chloride ion for the iodide ion

The crude iodide compound from (i) above was dissolved in methanol and passed rapidly through a prewashed IRA-410 (Cl⊖) column. The solvent was then removed under vacuum and the light yellow foam was chromatographed on silica gel employing as the eluent, a mixture of methylene chloride and methanol in a ratio of 22:3 by volume initially and then successively, a mixture of methylene chloride and methanol in increasing amounts of the latter, with elution taking place when the ratio of 4:1 by volume was reached. The eluted product was then concentrated to afford a white foam which was dissolved in ether, treated with decolorizing charcoal, filtered and concentrated to yield the title compound as a white solid, m.p., 45°-48° C.

PAIA Test—IC$_{50}$—2.0 μM
TEST A—IC$_{50}$—2.2 μM

What is claimed is:

1. A compound of formula I:

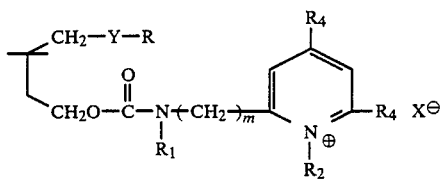     I wherein T is a group of the formula (a)

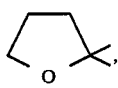  (a)

or a group of the formula (b)

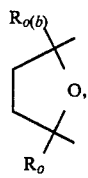

where both $R_o$'s are the same and are either hydrogen or methyl;

Y is —O— or

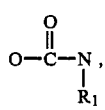

R is n-$C_{12}$–$C_{20}$alkyl, alkenyl or alkynyl;

each $R_1$, independently, is hydrogen, acetyl, pivaloyl, benzoyl or $C_1$–$C_4$alkyl;

m is an integer 1 to 8;

$R_2$ is methyl or ethyl;

each $R_4$, independently, is hydrogen or methyl;

and $X^\ominus$ is chloride, bromide, iodide or $C_1$–$C_4$alkyl-sulfonate.

2. A compound according to claim 1 of formula Ia:

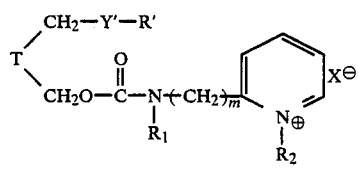  Ia wherein
Y' is

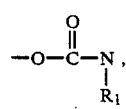

R' is n-$C_{12}$–$C_{20}$alkyl; and

T, m, $R_1$, $R_2$ and $X^\ominus$ are as defined in claim 1.

3. A compound according to claim 2 of formula Ib:

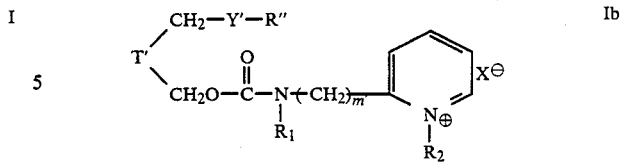  Ib where
T' is a group of formula (a) as defined in claim 1;
R'' is n-$C_{14}$–$C_{20}$alkyl;
m' is an integer 1 to 5; and
Y', $R_1$, $R_2$ and $X^\ominus$ are as defined in claim 2.

4. A compound according to claim 3 of formula Ic:

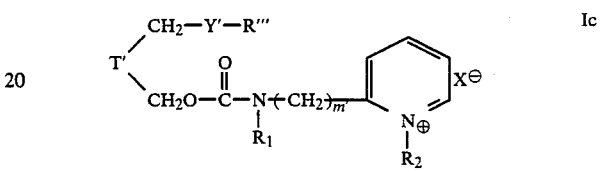  Ic where
R''' is n-$C_{16}$–$C_{20}$alkyl; and
T', Y', $R_1$, m', $R_2$ and $X^\ominus$ are as defined in claim 3.

5. A compound according to claim 4 having the formula

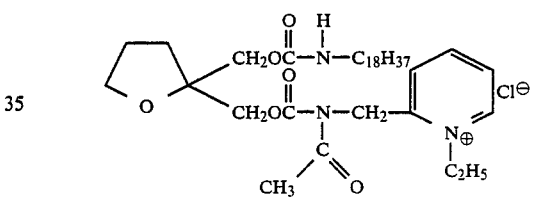

6. A compound according to claim 4 having the formula

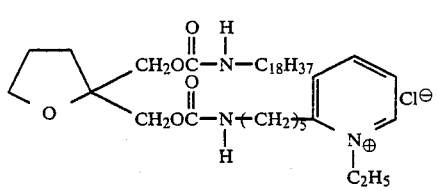

7. A method of inhibiting PAF-induced blood platelet aggregation comprising administering to a subject in need of such treatment a therapeutically effective amount of a compound according to claim 1.

8. A method according to claim 7 comprising administering a therapeutically effective amount of the compound of the formula

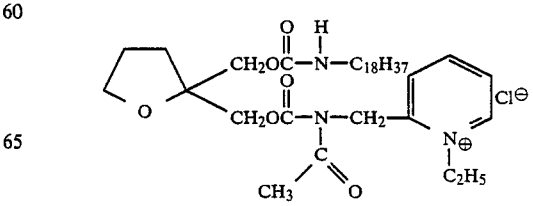

9. A method according to claim 7 comprising administering a therapeutically effective amount of the compound of the formula

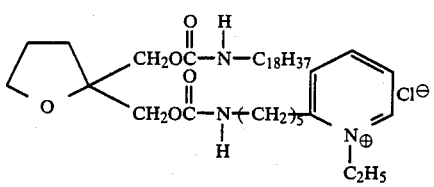

10. A method of inhibiting PAF-mediated bronchoconstriction comprising administering to a subject in need of such treatment a therapeutically effective amount of a compound according to claim 1.

11. A method according to claim 10 comprising administering a therapeutically effective amount of the compound of the formula

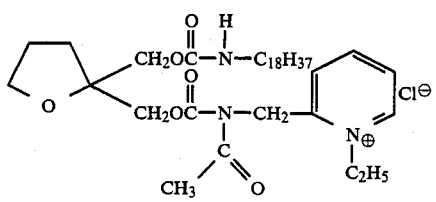

12. A method according to claim 10 comprising administering a therapeutically effective amount of the compound of the formula

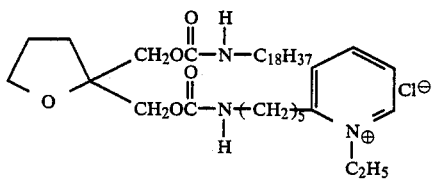

13. A method of inhibiting PAF-mediated extravasation comprising administering to a subject in need of such treatment a therapeutically effective amount of a compound according to claim 1.

14. A method according to claim 13 comprising administering a therapeutically effective amount of the compound of the formula

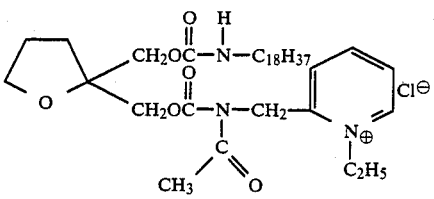

15. A method according to claim 13 comprising administering a therapeutically effective amount of the compound of the formula

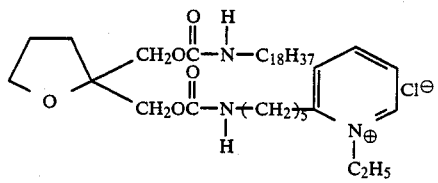

16. A method of inhibiting PAF-induced hypotension comprising administering to a subject in need of such treatment a therapeutically effective amount of a compound according to claim 1.

17. A method of inhibiting PAF-induced ischemic bowel disease comprising administering to a subject in need of such treatment a therapeutically effective amount of a compound according to claim 1.

18. A method of inhibiting PAF-mediated, endotoxin-induced lung injury comprising administering to a subject in need of such treatment a therapeutically effective amount of a compound according to claim 1.

19. A method of inhibiting PAF-mediated, endotoxin-induced septic shock comprising administering to a subject in need of such treatment a therapeutically effective amount of a compound according to claim 1.

20. A method of inhibiting PAF-mediated, endotoxin-induced adult respiratory distress syndrome comprising administering to a subject in need of such treatment a therapeutically effective amount of a compound according to claim 1.

21. A pharmaceutical composition useful in inhibiting PAF-induced blood platelet aggregation, PAF-mediated bronchoconstriction and extravasation, PAF-induced hypotension, PAF-induced ischemic bowel disease and PAF-mediated, endotoxin-induced lung injury comprising a pharmaceutically acceptable carrier and a therapeutically effective amount of a compound according to claim 1.

* * * * *